United States Patent
Evans et al.

(10) Patent No.: US 6,506,785 B2
(45) Date of Patent: Jan. 14, 2003

(54) TREATING OR PREVENTING THE EARLY STAGES OF DEGENERATION OF ARTICULAR CARTILAGE OR SUBCHONDRAL BONE IN MAMMALS USING CARPROFEN AND DERIVATIVES

(75) Inventors: Nigel A. Evans, East Lyme, CT (US); Carolyn R. Kilroy, Old Lyme, CT (US); Kristin M. Lundy, Groton, CT (US); Jean-Pierre Pelletier, St. Lambert (CA); Anthony P. Ricketts, Stonington, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/283,993

(22) Filed: Apr. 1, 1999

(65) Prior Publication Data

US 2001/0002401 A1 May 31, 2001

Related U.S. Application Data

(60) Provisional application No. 60/086,457, filed on May 22, 1998.

(51) Int. Cl.$^7$ .............................................. A61K 31/40
(52) U.S. Cl. .................................................... 514/411
(58) Field of Search ................................ 514/412, 411

(56) References Cited

U.S. PATENT DOCUMENTS 3,896,145 A * 7/1975 Berger et al. ................ 260/315

FOREIGN PATENT DOCUMENTS

| WO | 8402273 | 12/1983 |
| WO | 8603681 | 11/1985 |
| WO | 9221350 | 5/1991 |
| WO | 9850033 | 5/1998 |

OTHER PUBLICATIONS

Vasseur et al; J. Amer. Vet. Med. Assoc. (1995), vol. 206(6); pp. 807–811.*
Benton, et al., Am. J. Vet. Res. vol. 58, No.3, 1997, pp. 286–292, *Effect of carprofen on sulfated glycosaminoglycan metabolism, protein synthesis, and prostaglandin release by cultured osteoarthritic canine chondrocytes.*
Innes, J., In Practice, vol. 17, No. 3, 1995, pp. 102–109, *Diagnosis and treatment of osteoarthritis in dogs.*
Armstrong, S., Am. J. Vet. Res., vol. 60, No. 1, Jan. 1999, pp. 98–104, *Effects of R and S enantiomers and a racemic mixture of carprofen on the production and release of proteoglycan and prostaglandin E2 from equine chondrocytes and cartilage explants.*
Lust, G., et al., "Effects of Intramuscular Administration of Glycosaminoglycan Polysulfates on Signs of Incipient Hip Dysplasia in Growing Pups," *American Journal of Veterinary Research*, 53(10), 1836–1843 (1992).

McNamara, P.S., et al, "Slow–Acting Disease–Modifying Osteoarthritis Agents," *Osteoarthritis*, 27(4), 863–881 (1997).

(List continued on next page.)

*Primary Examiner*—Theodore J. Criares
(74) *Attorney, Agent, or Firm*—Kohn & Associates, PLLC; Paul H. Ginsburg; Lorraine B. Ling

(57) ABSTRACT

Treating or preventing the early stages of degeneration of articular cartilage or subchondral bone in the affected joint of a mammal is accomplished by administering a chondroprotective compound of Formula (I):

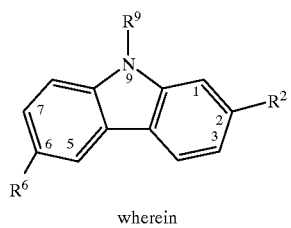

wherein

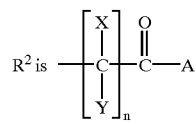

where A is hydroxy, $(C_1-C_4)$alkoxy, amino, hydroxy-amino, mono-$(C_1-C_2)$alkylamino, di-$(C_1-C_2)$alkylamino; X and Y are independently H or $(C_1-C_2)$alkyl; and n is 1 or 2; $R^6$ is halogen, $(C_1-C_3)$alkyl, trifluoromethyl, or nitro; $R^9$ is H; $(C_1-C_2)$alkyl; phenyl or phenyl-$(C_1-C_2)$alkyl, where phenyl is optionally mono-substituted by fluoro or chloro; —C(=O)—R, where R is $(C_1-C_2)$alkyl or phenyl, optionally mono-substituted by fluoro or chloro; or —C(=O)—O—R', where $R^1$ is $(C_1-C_2)$alkyl.

This treatment ameliorates, diminishes, actively treats, reverses or prevents any injury, damage or loss of articular cartilage or subchondral bone subsequent to said early stage of said degeneration. Whether or not a mammal needs such treatment is determined by whether or not it exhibits a statistically significant deviation from normal standard values in synovial fluid or membrane from the affected joint, with respect to at least five of the following substances: increased interleukin-1 beta (IL-1β); increased tumor necrosis factor alpha (TNFα); increased ratio of IL-1β to IL-1 receptor antagonist protein (IRAP); increased expression of p55 TNF receptors (p55 TNF-R); increased interleukin-6 (IL-6); increased leukemia inhibitory factor (LIF); decreased insulin-like growth factor-1 (IGF-1); decreased transforming growth factor beta (TGFβ); decreased platelet-derived growth factor (PDGF); decreased basic fibroblast growth factor (b-FGF); increased keratan sulfate; increased stromelysin; increased ratio of stromelysin to tissue inhibitor of metalloproteases (TIMP); increased osteocalcin; increased alkaline phosphatase; increased cAMP responsive to hormone challenge; increased urokinase plasminogen activator (uPA); increased cartilage oligomeric matrix protein; and increased collagenase.

6 Claims, No Drawings

OTHER PUBLICATIONS

Westacott, C.I., et al., "Cytokines in Osteoarthritis: Mediators or Markers of Joint Destruction," *Seminars in Arthritis and Rheumatism*, 25(4), 254–272 (1996).

Brandt, K.D., "Insights into the Natural History of Osteoarthritis Provided by the Cruciate–Deficient Mammal," *Annals of the New York of Sciences*, 732, 199–205 (1994).

Dean, D.D., et al., "Evidence for Metalloproteinase and Metalloproteinase Inhibitor Imbalance in Human Osteoarthritic Cartilage," *J. Clin. Invest.*, 84, 678–685 (1989).

Martel–Pelletier, et al., "Cytokines, Interleukin–1 and the Tumor Necrosis Factor in Human Osteoarthritic Tissues," *Trans. Orthrop. Res. Soc.*, 15, 111 (1990).

Martel–Pelletier, et al., "The Interleukin–1 Receptor in Normal and Osteoarthritic Human Articular Chondrocytes," *Arthritis & Rheumatism*, 35, 530–540 (1992).

Pelletier, J–P, et al., "Coordinate Synthesis of Stromelysin, Interleukin–1, and Oncogene Proteins in Experimental Osteoarthritis –An Immunohistochemical Study," *Am. J. Pathol.*, 142, 95–105 (1993).

Hilal, G., et al., "Osteoblast–Like Cells from Human Subchondral Osteoarthritic Bone Demonstrate an Altered Phentotype In Vitro," *Arthritis & Rheumatismi*, 41(5), 891–899 (1998).

Pelletier, J.P., et al., "Collagenolytic Activity and Collagen Matrix Breakdown of the Articular Cartilage in the Pond–Nuki Mammal Model of Osteoarthritis," *Arthritis Rheum.*, 26, 866–874 (1983).

Lajeunesse, D., et al., "Demonstration of an Osteoblast Defect in Two Cases of Human Malignant Osteoporosis: Correction of the Phenotype after Bone Marrow Transplant," *J. Clin. Invest.*, 98, 1835–1842 (1996).

Lajeunesse, D., et al., "Regulation of Osteocalcin Secretion by Human Primary Bone Cells and by the Human Osteosarcoma Cell Line MG–63, *Bone*, 14, 237–250 (1991).

Smith, et al., "Measurement of Protein Using Bicinchoninic Acid," *Anal Biochem*, 150, 76–85 (1985).

Leprince, et al., "Colorimetric Assay for the Simultaneous Measurement of Plasminogen Activators and Plasminogen Activator Inhibits in Serum–Free Conditioned Media from Cultured Cells," *Anal Biochem.*, 177, 341–346 (1989).

Mohan, S., et al., "Development of Valid Methods to Measure Insulin–Like Growth Factors–I and –II in Bone Cell–Conditioned Medium," *Endocrinology*, 126, 2534–42 (1990).

* cited by examiner

TREATING OR PREVENTING THE EARLY STAGES OF DEGENERATION OF ARTICULAR CARTILAGE OR SUBCHONDRAL BONE IN MAMMALS USING CARPROFEN AND DERIVATIVES

"This application claims the benefit of priority under 35 U.S.C. §119 of Ser. No. 60/086,457, filed May. 22, 1998."

The present invention relates to the use of carprofen in mammals as a means of treating and preventing cartilage and subchondral bone injury and loss in the inflamed joints of such mammals. Such damage to the cartilage and subchondral bone is a natural sequelae of the process of osteoarthritis and its aftermath when it occurs in the mammal. The ability of carprofen to achieve this unexpected result is referred to as "chondroprotection".

BACKGROUND OF THE INVENTION

Carprofen has been used heretofore as a COX-2 selective non-steroidal anti-inflammatory drug (NSAID) whose activity was based at least in part on the potent and selective inhibition of the inducible cyclooxygenase II (COX-2) isoenzyme. Such activity does not, however, exclude the possibility that carprofen, like other NSAIDs, possesses inhibitory activity with respect to the enzymes involved in the lipoxygenase pathway, or that it is active against the suppression, recruitment and migration of inflammatory cells and the release of enzymes and oxygen derived free radicals from such cells. While all of these activities would be understood in the art to have obvious relevance to the treatment of rheumatoid arthritis (RA), they would not be as clearly relevant to the treatment of osteoarthritis (OA). In fact, some NSAIDs are known to exacerbate the progress of OA and some pathologic cartilaginous and bone changes result from overuse of impaired joints as the result of NSAID-induced analgesia. This phenomenon is referred to as analgesic arthropathy.

OA has a complex multifactorial causality and considerable variability in its clinical expression, but synovial inflammation appears to be a key component of OA. Further, as a result of communication between synovial cells and cartilage cells (chondrocytes), synovial injury can stimulate the disaggregation of proteoglycans (PGs) and activated synovial cells produce an abundance of soluble factors, e.g., interleukin-1 (IL-1), tumor necrosis factor-$\alpha$ (TNF-$\alpha$), and prostaglandins, which can induce loss of articular cartilage. Direct injury to chondrocytes also stimulates matrix matelloprotease (MMP) activity, e.g., collagenases, stromelysins and gelatinases, and the production of various inflammatory mediators. In any event, decreased functionality of joint articular cartilage is fundamental to the pathogenesis of OA. Depletion of the PGs from the tissues of OA joints subjects the chondrocytes and cells of the subchondral bone and synovium to abnormal mechanical stresses because of the resilience which the PGs confer on cartilage.

Cartilage is basically a PG aggregate comprising a protein-carbohydrate complex whose filamentous structure is built from a single, long hyaluronic acid molecule to which extended core proteins are bonded noncovalently. These protein chains, in turn, have chondroitin sulfate and keratin sulfate chains bound to them covalently through serine side chains. Hyaluronic acid, chondroitin sulfate and keratin sulfate are all examples of glycosaminoglycans (GAGs), i.e., polysaccharides comprising polymers of repeating disaccharide units in which one of the sugars is either N-acetylgalactosamine or N-acetylglucosamine. In cartilage the PG structure binds collagen and helps to hold the collagen fibers in a tight, strong network. Collagen fibers, in turn, are formed from the basic tropocollagen molecule, which is a triple helix of three polypeptide chains, each about 1000 residues in length.

Metabolic processes continuously occur in any given joint that are necessary for its repair and normalization subsequent to its being subjected to an insult such as a traumatic injury. Accordingly, in order for a compound to be an acceptable chondroprotective agent it must first of all be capable of sustaining such chondrocyte metabolic activity, i.e., of not inhibiting or interfering with the cellular replication and biosynthesis of matrix components which are part of the healing process. In this regard, the artisan will recognize that many NSAIDs display a marked inhibitory action on the biosynthesis of the principal components of the extracellular matrix. At the same time an acceptable chondroprotective agent must be capable of counteracting the degradative action of mediators such as various cytokines, prostaglandins and proteinases on the cartilage. Accordingly, it has been accepted in the art that potential chondroprotective drugs should be evaluated both as to their positive effects on anabolic pathways as well as to their ability to inhibit catabolic processes. Catabolic events which have typically been monitored include, inter alia, the release and inhibition of matrix degrading enzymes, effects on prostaglandin and leukotriene biosynthesis, and the ability of the test drug to inhibit IL-1 mediated degradation of articular cartilage. Anabolic events which have been studied have commonly included the ability of a test drug to stimulate the synthesis of protein, collagen, PGs, and hyaluronic acid (HA).

While the term "chondroprotective agent" as used herein will be understood to refer to those compounds whose chief site of action is the cartilage, it will also be appreciated that such chondroprotective agents may also possess anti-inflammatory action with regard to the synovium, may positively impact the biosynthesis of cells in subchondral bone and other connective tissues such as synovial fibroblasts, and may mediate inflammatory cell migration so as to impede the inflammatory process.

The present invention is applicable to all mammals generally because of the significant extent to which their shared evolution and embryogenic congruity produce similar cells, tissues and organ systems with homologous genetic codes that express comparable protein entities which operate in equivalent metabolic pathways. Mammals of all types are included within the scope of the present invention, since even the rarest of these may be held in captivity in a zoological institution and require the therapy provided by the present invention. It is preferred, however, that the present invention be directed to more numerous and economically significant species such as cats, dogs, cattle and bison, horses, pigs, sheep and goats. Some of these species are more susceptible or prone to problems of articular cartilage degeneration and loss than others. Thus, the therapy provided by the present invention is especially directed to cats, dogs and horses.

DESCRIPTION OF THE STATE OF THE ART

Commercial preparations which have been examined heretofore as potential chondroprotective agents include tiaprofenic acid, diclofenac sodium, tribenoside, pentosan polysulfate sodium, Arteparon® (a trademark of Luitpold-Werk, Munich, Germany), and Rumalon® (a trademark of Robapharm Limited, Basel, Switzerland). The diverse structures of these agents may be demonstrated or explained in the following manner:

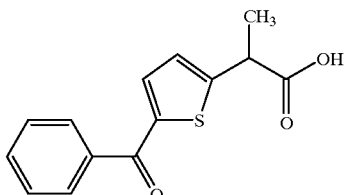

tiaprofenic acid

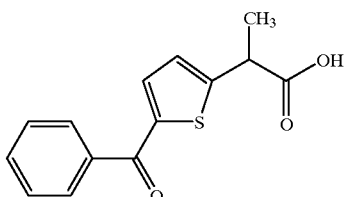

tiaprofenic acid

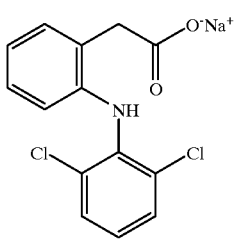

diclofenac sodium

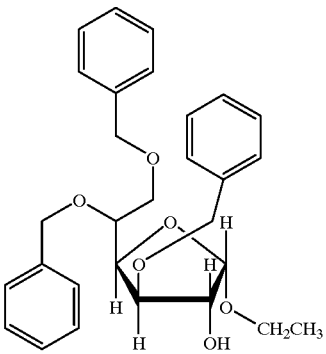

tribenoside
tribenoside

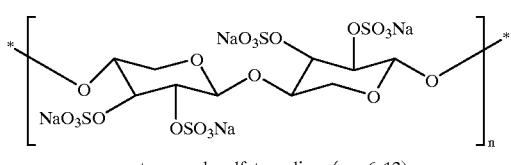

pentosan polysulfate sodium (n = 6-12)

None of the above-described compounds would in any way suggest carprofen and the carprofen derivatives used in the methods of treatment of the present invention.

Lust, G.; Williams, A. J.; Burton-Wurster, N.; Beck, K. A.; and Rubin, G.; "Effects of Intramuscular Administration of Glycosaminoglycan Polysulfates on Signs of Incipient Hip Dysplasia in Growing Pups", *American Journal of Veterinary Research,* 53(10), 1992, 1836–1843, treated growing pups susceptible to hip dysplasia with GAG polysulfates available as Adequan® from Luitpold-Werk, Munich, Germany. Hip joints were examined radiographically and intra-articular tissues were evaluated macroscopically and biochemically. Lust et al. concluded that although there was a significant reduction of cartilage fibronectin content, the proteoglycan content and the observed joint pathologic score means were not statistically different between control and treated pups. An earlier study using the same drug was noted that had reported reduction in cartilage degeneration, inhibition of proteases, and promotion of proteoglycan formation in stifles of dogs when cruciate ligaments had been resected to create an unstable stifle, with subsequent development of osteoarthritis.

The precise mechanism of action of carprofen and the carprofen derivatives used in the methods of treatment of the present invention is not well understood, but it is considered unlikely that it would have anything in common with the supposed mechanisms of action by which GAG polysulfates operate.

McNamara, P. S.; Johnston, S. A.; and Todhunter, R. J.; "Slow-Acting Disease-Modifying Osteoarthritis Agents", *Osteoarthritis,* 27(4), 1997, 863–881, studied the disease-modifying effectiveness of oral products considered to be nutritional supplements, e.g., polysulfated glycosaminoglycan (PSGAG), as to whether they had a positive effect on cartilage matrix synthesis and hyaluronan (HA) synthesis by the synovial membrane, as well as an inhibitory effect on catabolic enzymes in osteoarthritic joints. Favorable modification of the painful clinical signs of osteoarthritis by nutritional supplement products containing glucosamine and chondroitin sulfate (CS) were found to be supported only by anecdotal evidence, and not by any scientific evaluation. Regarding hyaluronic acid (HA), one study was noted in which atrophied mammal articular cartilage was treated with HA and a chondrostabilizing effect was obtained. It was hypothesized that the HA acted through down-regulation of tumor necrosis factor-$\alpha$ (TNF-$\alpha$). Based on these results, HA was regarded as a potential form of therapy for OA in mammals. It was further concluded that PSGAG would be a useful adjunctive treatment for OA if administered early, based on a study showing disease-modifying effect on cartilage homeostasis, based on decreased microscopic structural alteration, retention of proteoglycan in cartilage, and decreased proteinase activity when compared with activity in control joints. Pentosan polysulfate (PPS) was found to significantly decrease articular cartilage damage, based on gross and histologic evaluation and maintenance of normal articular cartilage proteoglycan content. The tetracyclines doxycycline and minocycline may provide a disease-modifying effect because of their ability to inhibit the activity of metalloproteinases, collagenase, and gelatinase.

The above-described pleiotropic effects on joint tissues obtained with the various treatment agents discussed may be obtained through mechanisms of action one or more of which is shared in common with carprofen and the carprofen derivatives used in the methods of treatment of the present invention. However, because of their great structural dissimilarity, none of these agents would in any way suggest carprofen and the carprofen derivatives of the present invention.

Benton, H. P.; Vasseur, P. B.;Broderick-Villa, G. A.; and Koolpe, M.; "Effect of Carprofen on Sulfated Glycosaminoglycan Metabolism, Protein Synthesis, and Prostaglandin Release by Cultured Osteoarthritic Mammal Chondrocytes", *American Journal of Veterinary Research,* 58(3), 1997, 286–292, after noting that the anti-inflammatory effects of carprofen are likely to be mediated by a principal mode of action unrelated to the cyclo-oxygenase enzyme inhibition that is the major mechanism associated with NSAID activity, advise consideration of the direct effects on bone and cartilage metabolism of NSAIDs used for treatment of arthritis. Such NSAIDs as aspirin and indomethacin suppress joint swelling and the infiltration of inflammatory cells into the joint cavity, but at the same time such NSAIDs may stimulate IL-1 activity, and the action of this cytokine may in turn result in the stimulation of matrix degradation and the inhibition of new matrix synthesis. Thus, upregulation of IL-1 may have long-term adverse effects on cartilage maintenance. Using cell cultures of mammal cartilage explants and measuring the effect of carprofen on GAG synthesis and degradation, protein synthesis, cell viability and prostaglandin release, it was found that carprofen concentrations of 1 and 10 µL/ml had a potentially beneficial effect on cartilage matrix maintenance by selectively stimulating new cartilage GAG synthesis without any direct effect on cartilage proteoglycan breakdown. However, the need for further studies was acknowledged.

As demonstrated by the above-discussed technical literature, much interest has centered on the role of cytokines in joint disease, since articular cartilage integrity is maintained by the balance between cytokine-driven anabolic and catabolic processes. However, the specific contribution of cytokine action to the pathophysiology of OA is not well understood. See Westacott, C. I. and Sharif, M.; "Cytokines in Osteoarthritis: Mediators or Markers of Joint Destruction?", *Seminars in Arthritis and Rheumatism*, 25(4), 1996, 254–272.

A variety of assays and animal models have been developed in the art in order to elucidate the multifactorial character of articular cartilage degeneration and the many mechanisms of action by which it proceeds. One of the more important of these animal models is the cruciate-deficient mammal knee model in which the anterior cruciate ligament of the left knee of a mammal subject is transected, while the right knee joint is not operated on and is left as a normal control. The stress thus induced in the mammal left knee joint eventually produces osteoarthritis, but there is also produced a substantial repetition of the very earliest pathologic changes in the mammal joint, especially with respect to changes in the character of the subchondral bone and degeneration of the overlying articular cartilage. For a discussion of some of the studies which have been carried out using the cruciate-deficient mammal model, see Brandt, K. D., "Insights into the Natural History of Osteoarthritis Provided by the Cruciate-Deficient Mammal", *Annals of the New York Academy of Sciences*, 732, 1994, 199–205.

Additional investigations which have used the cruciate-deficient mammal model and other assays to shed more light on the early changes in articular cartilage degeneration and osteoarthritis and the mechanisms of action responsible for these changes, are described in the following articles from the technical literature:

Dean, D. D.; Martel-Pelletier, J.; Pelletier, J-P.; Howell, D. S.; Woessner, J. F., Jr.; "Evidence for Metalloproteinase and Metalloproteinase Inhibitor Imbalance in Human Osteoarthritic Cartilage", *J. Clin. Invest.*, 84, 1989, 678–685;

Martel-Pelletier, J.; Cloutier, J-M.; Pelletier, J-P.; "Cytokines, Interleukin-1 and the Tumor Necrosis Factor in Human Osteoarthritic Tissues", *Trans. Orthrop. Res. Soc.*, 15, 1990, 111;

Martel-Pelletier, J.; McCollum, R.; DiBattista, J.; Faure, M-P.; Chin, J. A.; Fournier, S.; Sarfati, M.; Pelletier, J-P.; "The Interleukin-1 Receptor in Normal and Osteoarthritic Human Articular Chondrocytes", *Arthritis & Rheumatism*, 35, 1992, 530–540;

Pelletier, J-P.; Faure, M-P.; DiBattista, J. A.; Wilhelm, S.; Visco, D.; Martel-Pelletier, J.; "Coordinate Synthesis of Stromelysin, Interleukin-1, and Oncogene Proteins in Experimental Osteoarthritis—An Immunohistochemical Study", *Am. J. Pathol.*, 142, 1993, 95–105; and Hilal, G.; Martel-Pelletier, J.; Pelletier, J-P.; Ranger, P.; Lajeunesse, D.; "Osteoblast-Like Cells from Human Subchondral Osteoarthritic Bone Demonstrate an Altered Phenotype In Vitro", *Arthritis & Rheumatism*, 41(5), 1998, 891–899.

SUMMARY OF THE INVENTION

In accordance with the present invention there is provided a method of treating or preventing the early stages of degeneration of articular cartilage or subchondral bone in one or more joints of a mammal in need of such treatment, comprising (1) establishing the status of said mammal as presently or prospectively being in said early stages and thus in need of such treatment; and thereupon (2) administering to said mammal an amount therapeutically effective for treating or preventing said early stages of degeneration of articular cartilage or subchondral bone, of a chondroprotective compound of Formula (I):

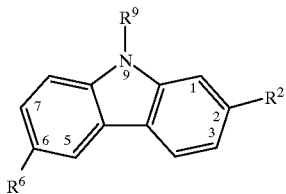

Formula (I)

wherein:

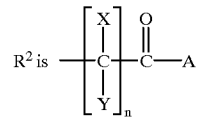

where A is hydroxy, $(C_1-C_4)$alkoxy, amino, hydroxy-amino, mono-$(C_1-C_2)$alkylamino, di-$(C_1-C_2)$alkylamino; X and Y are independently H or $(C_1-C_2)$alkyl; and n is 1 or 2;

$R^6$ is halogen, $(C_1-C_3)$alkyl, trifluoromethyl, or nitro;

$R^9$ is H; $(C_1-C_2)$alkyl; phenyl or phenyl-$(C_1-C_2)$alkyl, where phenyl is optionally mono-substituted by fluoro or chloro; —C(=O)—R, where R is $(C_1-C_2)$alkyl or phenyl, optionally mono-substituted by fluoro or chloro; or —C(=O)—O-$R^1$, where $R^1$ is $(C_1-C_2)$alkyl;

where X and Y are different, the (−)(R) and (+)(S) enantiomers thereof; and all pharmaceutically acceptable salt forms, prodrugs and metabolites thereof which are therapeutically active for treating or preventing said early stages of degeneration of articular cartilage or subchondral bone. Where the chondroprotective compound of Formula (I) exists as (−)(R) and (+)(S) enantiomers, in accordance with the present invention there is provided the (+)(S) enantiomer alone, or where both enantiomers are present together, there is provided a racemic or a non-racemic mixture thereof.

There is also provided the above-described method wherein said mammal is preferably a cat, dog or horse, and said treatment or prevention ameliorates, diminishes, actively treats, reverses or prevents any injury, damage or loss of articular cartilage or subchondral bone subsequent to said early stages of said degeneration.

There is further provided in accordance with the present invention the abovedescribed method of treating or preventing the early stages of degeneration of articular cartilage or subchondral bone in one or more joints of a mammal, preferably a cat, dog, or horse, in need of such treatment, wherein the status of said mammal as presently or prospectively being in said early stages and thus in need of such treatment is determined by (1) positive results from the clinical examination and evaluation of the joints of said mammal, including measurement of hip dysplasia progression; (2) performance of any invasive surgical procedure on one or more joints of said mammal; (3) positive results from an examination of one or more joints of said mammal using noninvasive procedures including radiographic and magnetic resonance imaging (MRI); or (4) positive results from any biochemical test performed on body fluids or joint tissue of said mammal with respect to one or more of the following substances: increased interleukin-1 beta (IL-1β); increased tumor necrosis factor alpha (TNFα); increased ratio of IL-1β to IL-1 receptor antagonist protein (IRAP); increased expression of p55 TNF receptors (p55 TNF-R); increased interleukin-6 (IL-6); increased leukemia inhibitory factor (LIF); unchanged or decreased insulin-like growth factor-1 (IGF-1); decreased transforming growth factor beta (TGFβ); unchanged or decreased platelet-derived growth factor (PDGF); unchanged or decreased basic fibroblast growth factor (b-FGF); increased keratan sulfate; increased matrix metalloproteases (MMPs) including stromelysin; increased ratio of matrix metalloproteases (MMPs) including stromelysin, to tissue inhibitor of metalloproteases (TIMP); increased osteocalcin; increased alkaline phosphatase; increased cAMP responsive to hormone challenge; increased urokinase plasminogen activator (uPA); increased cartilage oligomeric matrix protein; and increased collagenase.

It is also within the scope of the present invention to carry out the above-described method of treating or preventing the early stages of degeneration of articular cartilage or subchondral bone in one or more joints of a mammal by administering combinations of compounds, comprising more than one member selected from the above-recited group of chondroprotective compounds of Formula (I); or one or more said chondroprotective compounds of Formula (I) with one or more members selected from the group consisting essentially of polysulfated glycosaminoglycan (PSGAG), glucosamine, chondroitin sulfate (CS), hyaluronic acid (HA), pentosan polysulfate (PPS), doxycycline, and minocycline.

There is further provided the above-described methods wherein said therapeutically effective amount of a chondroprotective compound of Formula (I) as defined, and especially of said (+)(S)-enantiomer of 6-chloro-α-methyl-9H-carbazole-2-acetic acid, is administered systemically to said mammal wherein said systemic administration comprises: (1) injection or infusion into suitable body tissues or cavities of a pharmaceutical composition containing said chondroprotective compound in suitable liquid form for intramuscular or intravenous delivery thereof; or for serving as a depot for delivery thereof; (2) instillation into suitable body tissues or cavities of a pharmaceutical composition containing said chondroprotective compound in suitable solid form for serving as a solid implant composition for delayed-, sustained-, and/or controlled-release delivery thereof; or (3) ingestion of a pharmaceutical composition containing said chondroprotective compound in suitable solid or liquid form for peroral delivery thereof.

There is further provided the above-described method of treating or preventing the early stages of degeneration of articular cartilage or subchondral bone comprising ingestion or administration of a solid peroral dosage form selected from the group consisting of delayed-release or sustained-release oral tablets, capsules and microparticulates which provide systemic delivery of the active ingredient in a controlled manner over at least a 10-hour period There is still further provided the above-described methods wherein said therapeutically effective amount of said chondroprotective compound of Formula (I) is administered locally comprising: (1) injection or infusion into a local site in the early stages of degeneration of articular cartilage or subchondral bone of a pharmaceutical composition containing said chondroprotective compound in suitable liquid form for intraarticular, intrachondrial, intracostal, intraosteal, intrapelvic, intraspinal, intrasternal, intrasynovial, or intratarsal delivery thereof, including components which provide delayed-release, controlled-release, and/or sustained-release of said chondroprotective compound into said local site; or for serving as a depot for delivery thereof wherein said composition provides storage of said chondroprotective compound and thereafter delayed-, sustained-, and/or controlled-release thereof; or (2) instillation of a pharmaceutical composition containing said chondroprotective compound in suitable solid form for serving as a solid implant for delivery thereof, said composition optionally providing delayed-, sustained-, and/or controlled-release of said chondroprotective compound to said local site.

There is still further provided the above-described methods wherein the therapeutically effective amount of said chondroprotective compound is administered to said mammal in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day. Administration of 6-chloro-α-methyl-9H-carbazole-2-acetic acid is typically provided by dosing at a rate of about 4.0 mg/kg/day.

There is additionally provided in accordance with the present invention a pharmaceutical composition for treating or preventing the early stages of degeneration of articular cartilage or subchondral bone in the joints of a mammal in need of such treatment, comprising a pharmaceutically acceptable carrier together with an amount therapeutically effective for treating or preventing said early stages of degeneration of articular cartilage or subchondral bone, of a chondroprotective compound of Formula (I) as above-defined.

There is further provided the above-described pharmaceutical composition wherein said chondroprotective compound is a compound of Formula (I) wherein one of X and Y is H and the other is methyl; and wherein when both resulting enantiomers are present, (+)(S) enantiomer is present in amount of at least 75%. In particular, there is provided the above-described pharmaceutical composition wherein for Formula (I), for $R^2$, n=1, one of X and Y is H and the other is methyl, and A is hydroxy, ($C_1$–$C_2$) alkoxy, or amino; $R^6$ is chloro or trifluoromethyl; and $R^9$ is H, methyl, acetyl, benzoyl, or acetyloxy; and wherein when both resulting enantiomers are present together, (+)(S) enantiomer is present in amount of at least 85%, preferably at least 90%, more preferably at least 95%, and most preferably at least 99%.

There is still further provided the above-described pharmaceutical compositions in which said chondroprotective compound comprises 6-chloro-α-methyl-9H-carbazole-2-acetic acid; and wherein when both resulting enantiomers are present together, (+)(S) enantiomer is present in an amount of at least 85%, preferably at least 90%, more preferably at least 95%, and most preferably at least 99%. In particular, there is provided the above- and below-described pharmaceutical composition in which said inhibitor is comprised entirely of (+)(S) enantiomer of 6-chloro-α-methyl-9H-carbazole-2-acetic acid.

There is also provided the above-described pharmaceutical compositions wherein the therapeutically effective amount of chondroprotective compound of Formula (I) is sufficient, in the context of the dosage regimen and administration parameters employed, to provide a member being treated with an amount of said chondroprotective compound, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day. Administration of 6-chloro-α-methyl-9H-carbazole-2-acetic acid is typically provided by dosing at a rate of about 4.0 mg/kg/day.

There is further provided the above-described pharmaceutical compositions wherein said therapeutically effective amount of chondroprotective compounds of Formula (I) is provided in a dosage form suitable for systemic administration which comprises: (1) injection or infusion into suitable body tissues or cavities of said pharmaceutical composition containing said chondroprotective compound in suitable liquid form for intramuscular or intravenous delivery thereof; or for serving as a depot for delivery thereof; (2) instillation into suitable body tissues or cavities of said pharmaceutical composition containing said chondroprotective compound in suitable solid form for serving as a solid implant for delivery thereof, said composition optionally providing for delayed-, sustained-, and/or controlled-release delivery thereof; or (3) ingestion of said pharmaceutical composition containing said chondroprotective compound in suitable solid or liquid form for peroral delivery thereof.

There is still further provided the above-described pharmaceutical compositions wherein said therapeutically effective amount of chondroprotective compound of Formula (I) is provided in a dosage form suitable for local administration which comprises (1) injection or infusion into a local site in the early stages of degeneration of articular cartilage or subchondral bone in suitable liquid form for intraarticular, intrachondrial, intracostal, intraosteal, intrapelvic, intraspinal, intrasternal, intrasynovial, or intratarsal delivery thereof, including components which provide delayed-release, controlled-release, and/or sustained-release of said chondroprotective compound; or for serving as a depot for delivery thereof wherein said composition provides storage of said chondroprotective compound and thereafter delayed-, sustained-, and/or controlled-release thereof into said local site; or (2) installation of said pharmaceutical composition in suitable solid form for serving as a solid implant composition for delivery thereof, said composition optionally providing delayed-, sustained-, and/or controlled-release thereof.

Particular dosage forms of the above-described pharmaceutical compositions include solid peroral dosage forms selected from the group consisting of delayed-release oral tablets, capsules, caplets, and multiparticulates which prevent release and absorption in the stomach to facilitate delivery distal to the stomach of the mammal, and sustained-release oral tablets, capsules and microparticulates which provide systemic delivery of the active ingredient in a controlled manner up to a 24-hour period.

There is provided in accordance with the present invention combinations of one or more other therapeutically active agents together with the chondroprotective compounds of Formula (I) which make up the above-described pharmaceutical compositions of the present invention. It is provided that where a joint has become seriously infected at the same time by microorganisms, e.g., bacteria, fungi, protozoa, virus and the like, the active ingredient of the present invention will desirably be administered in combination with one or more antibiotic, antifungal, antiprotozoal, antiviral or similar therapeutic agents. Further, the chondroprotective compounds of Formula (I) may be administered in combination with one or more members selected from the group consisting essentially of the classes of inhibitors and examples thereof comprising $H_1$-receptor antagonists; kinin-$B_1$- and $B_2$-receptor antagonists; leukotriene $LTC_4$-, $LTD_4/LTE_4$-, and $LTB_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids, e.g., dexamethasone; broad-spectrum antiparasitic antibiotics, e.g., the avermectins and the milbemycins; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone. It is further provided that the chondroprotective compounds of Formula (I) may be administered in combination with therapeutic agents intended for the treatment of disease conditions, syndromes and symptoms found in older mammals, comprising one or more members selected from the group consisting essentially of cognitive therapeutics to counteract memory loss and impairment; antidyskinetic/antiparkinsonian agents, e.g., selegeline; anti-hypertensives and other cardiovascular drugs intended to offset the consequences of atherosclerosis, including hypertension, myocardial ischemia including angina, congestive heart failure, and myocardial infarction, selected from diuretics, vasodilators such as hydralazine, β-adrenergic receptor antagonists such as propranolol, angiotensin-II converting enzyme inhibitors (ACE-inhibitors) such as enalapril used to treat geriatric mammals with mitral insufficiency, and enalapril alone and in combination with neutral endopeptidase inhibitors, angiotensin II receptor antagonists such as losartan, renin inhibitors, calcium channel blockers such as nifedipine, sympatholytic agents such as methyldopa, $α_2$-adrenergic agonists such as clonidine, α-adrenergic receptor antagonists such as prazosin, and HMG-CoA-reductase inhibitors (anti-hypercholesterolemics) such as lovastatin or atorvastatin; antineoplastic agents, especially antimitotic drugs including the vinca alkaloids such as vinblastine and vincristine; growth hormone secretagogues; strong analgesics; local and systemic anesthetics; and $H_2$-receptor antagonists and other gastroprotective agents.

It is still further provided that the above combinations of therapeutic agents are used to treat acute conditions in mammals, including bacterial infections occurring simultaneously with the early stages of degeneration of articular cartilage or subchondral bone; and to treat chronic conditions in mammals, wherein the regimen used for this purpose comprises administration of the chondroprotective compounds of the present invention in combination with other medications used on a regularly scheduled basis for treating chronic conditions; formulation of the chondroprotective compounds of the present invention with one or more other therapeutic agents which are to form the intended combination, into a convenient dosage form containing all of the drugs forming the combination, including wherein said different drugs have varying half-lives, by creating controlled-release forms of said drugs with different release times which achieves relatively uniform dosing; a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the mammal being treated, even though the individual drugs making up said combination are not being administered to said mammal simultaneously.

It is also contemplated that in accordance with the present invention there will also be provided a package suitable for use in commerce for treating or preventing the early stages of degeneration of articular cartilage or subchondral bone in one or more joints of a mammal in need of such treatment, comprising a suitable outer carton and an inner container removably housed therein; enclosed in said container a suitable dosage form of a chondroprotective compound of Formula (I) as described hereinabove; and associated with said carton or container printed instructional and informational material, which may be attached to said carton or to said container enclosed in said carton, or displayed as an integral part of said carton or container, said instructional and informational material stating in words which convey to a reader thereof that said active ingredient, when administered to a mammal in the early stages of degeneration of articular cartilage or subchondral bone in one or more joints thereof, will ameliorate, diminish, actively treat, reverse or prevent any injury, damage or loss of articular cartilage or subchondral bone subsequent to said early stages of said degeneration. In a preferred embodiment said package comprising carton and container as above-described will conform to all regulatory requirements relating to the sale and use of drugs for the treatment of animals, including especially said instructional and informational material.

It is also contemplated that in accordance with the present invention there will further be provided a package of the type described immediately above, comprising a suitable container as described; enclosed in said container an oral dosage form of a chondroprotective compound of Formula (I); and associated with said container printed instructional and informational material as above-described.

DETAILED DESCRIPTION OF THE INVENTION

The object of the present invention is to provide methods of treatment, and pharmaceutical compositions useful therein as well as suitable packaging therefor, which are applicable to mammals which in the future may suffer from injury, damage or loss of articular cartilage or subchondral bone in one or more joints of such a mammal. Cats, dogs and horses among mammals are especially vulnerable to inflammatory diseases and processes such as rheumatoid arthritis, osteoarthritis, traumatic or degenerative joint disease, use of impaired joints, actual or incipient hip dysplasia, and osteochondrosis. An important concomitant of these inflammatory diseases and processes is actual or prospective damage to or erosion of the articular cartilage and subchondral bone present in the joints of such felines, canines, and equines which have or may become inflamed.

Inflammation in mammals can be treated by the administration of a non-steroidal anti-inflammatory drug (NSAID), e.g., ARQUEL®, meclofenamic acid, although only two therapeutic agents of this type have been approved by the Food and Drug Administration, Committee on Veterinary Medicine (FDA/CVM), for use in dogs in the United States. A much greater variety of NSAIDs have been approved for use in humans, and they have therefore provided substantially greater efficacy and safety data from clinical trials and investigatory scrutiny. Accordingly, conclusions about the modes of action and other pharmacological aspects of the action of NSAIDs in a veterinary context, especially for use in treating non-human mammals, are often extrapolated from experience in human mammals. The description herein takes similar advantage of the high degree of physiological commonality between these mammalian species to demonstrate many of the underlying aspects of the present invention.

Treating mammals with anti-inflammatory agents is especially troublesome in two regards. First, the pathologic changes in cartilage and subchondral bone in the joints of mammals most prevalently accompanies osteoarthritis, which is a multifactorial and variably expressed disease which is still not fully understood, making decisions about appropriate therapy often difficult. For example, although some degree of synovial inflammation appears to be a common component of osteoarthritis, this inflammation has been regarded as arising from the effects of immunogens released during cartilage breakdown. More recently, however, this paradigm has been questioned. Second, long-term application of most NSAIDs, especially those more established in use, may actually exacerbate the progress of osteoarthritis. In light of these problems and uncertainties, the discovery of the present invention is all the more surprising, that the chondroprotective compounds of Formula (I) are useful in treating or preventing such articular cartilage damage while simultaneously having no adverse impact on the course of inflammation in the mammal joint involved. This and other aspects of the present invention will be better understood from the description in the below paragraphs of those features and characteristics of cartilage in the mammal joint which are especially relevant to the methods of treatment of the present invention.

Cartilage is a fibrous connective tissue existing in several forms, e.g., hyaline cartilage, elastic cartilage, and fibrocartilage. Hyaline cartilage is a somewhat elastic, semitransparent substance with an opalescent bluish tinge, composed of basophilic, fibril-containing interstitial substance with cavities (lacuna) in which the chondrocytes, mature cartilage cells, occur. It is a highly specialized connective tissue comprising water, collagen and proteoglycans which together create a unique fiber-reinforced water gel which is stiff but resilient and has considerable shock-absorbing capacity. The proteoglycan (PG) component is a protein-carbohydrate complex which has a filamentous structure. The core of this filamentous structure is a single long molecule of hyaluronic acid, which is a glycosaminoglycan (GAG), i.e., a polymer of repeating disaccharide units in which one of the sugars is either N-acetylgalactosamine or N-acetylglucosamine. In hyaluronic acid, e.g., the repeating disaccharide unit comprises the monosaccharide derivative N-acetylglucosamine having a glycosidic bond $\beta(1 \rightarrow 4)$ to the monosaccharide derivative glucuronic acid, which in turn has a glycosidic bond α(1→3) to the next N-acetylglucosamine unit of the repeating disaccharide.

To the hyaluronic acid filamentous core of cartilage, in turn, there are bound noncovalently, with the aid of a "link protein", a regular series of extended core proteins comprising collagen. The basic unit of collagen is the tropocollagen molecule, a triple helix of three polypeptide chains about 1000 residues in length each. To each of these extended core collagen molecules, in turn, there is bound through a serine side chain a regular series of chondroitin sulfate and keratan sulfate chains. Chondroitin sulfate and keratan sulfate are also examples of glycosaminoglycan (GAG) polymers similar to hyaluronic acid as above-described, in which for the polymer of repeating disaccharide units one of the sugars must be GalNAc-6s, i.e., N-acetylgalactosamine having a sulfate group on carbon 6. The glycosaminoglycans which are components of the cartilage structure are polysaccharides in which the sugar residues are modified to produce polymers which have a wide variety of properties that approach polypeptides in their structural complexity. Accordingly, it can be seen that articular cartilage, i.e., cartilage to be found in the joints of mammals, consists of a very elaborate and complex molecular structure. In order to understand the manner in which the methods and compositions of the present invention address the problem of cartilage injury and loss, however, it will also be necessary to examine the makeup of cartilage and its environment in the joint on a macroscopic scale, in addition to the just-recited study on a microscopic scale.

As above-described, articular cartilage comprises the living cells (chondrocytes) which generate and are surrounded by the interstitial material generally referred to as the extracellular matrix. Since osteoarthritis is defined as the failure of the diarthrodial (movable, synovial-lined) joint, it follows that in such a joint there will always be found at least two movable bony surfaces that would meet but for the fact that they are surrounded by the synovial membrane, which secretes synovial fluid, a transparent alkaline viscid fluid which fills the joint cavity, and articular cartilage, which is interposed between the articulating bony surfaces, usually in place of the synovial membrane at that point.

The earliest gross pathologic finding in osteoarthritis is softening of the articular cartilage in habitually loaded areas of the joint surface, which in the case of the knee joint of the mammal, especially in models of osteoarthritis involving transection of the cruciate ligament in the knee joint, consists of the femoral condyle and the tibial plateau. With progression of osteoarthritis the integrity of the cartilage surface is lost and the articular cartilage thins, with vertical clefts extending into the depth of the cartilage in a process called fibrillation. Joint motion may cause fibrillated cartilage to shed segments that expose the bone underneath (subchondral), which then undergoes sclerosis. Subchondral cysts also develop which may be filled with synovial fluid. At the joint margins osteophytes (bone spurs) form.

Changes in the subchondral bone also play a role in the pathology of cartilage destruction. Studies of the joints of mammals, especially dogs, which have undergone anterior cruciate ligament transection reveals subchondral sclerosis and osteopenia, i.e., bone loss in the subchondral trabeculae. Subsequent to these changes, there is a thickening of the subchondral plate. The loss of subchondral bone increases the mechanical strain on the overlying articular cartilage, leading to its degeneration. The subsequent thickening of the subchondral plate negatively affects intrinsic repair mechanisms and thereby contributes to the progression of cartilage breakdown.

The breakdown of the extracellular matrix of the cartilage is accompanied by mitotic division of the chondrocytes which then form in clusters. There is a reduction in the glycosaminoglycan components of the cartilage and patchy proteoglycan depletion. In many areas fibrocartilage, characterized by an extracellular matrix of thick, compact parallel collagenous bundles, replaces hyaline cartilage. However, it should be noted that these and the above-described pathologic changes in the articular cartilage are characteristic of later stages of osteoarthritis, and that hypertrophy, i.e., thickening of the articular cartilage occurs first, as shown by the cruciate-deficient mammal, especially dog knee joint model. Cartilage thickening results from increased water content, an increase in proteoglycan synthesis, and an increase in both the content and concentration of proteoglycans in the articular cartilage. This stage of hypertrophic repair of the articular cartilage may persist for some time, but the repair cartilage tissue which is formed lacks the resiliency and resistance to mechanical stress possessed by normal hyaline cartilage. Eventually, proteoglycan production subsides and the chondrocytes are no longer able to maintain their extracellular matrix. This end stage results in full-thickness loss of articular cartilage.

Synovitis, i.e., inflammation of the synovium, the synovial membrane, can contribute to the pathology of cartilage injury and loss. Synovial inflammation is characterized by extensive infiltration of the synovial fluid by mono-nuclear cells, by synovial membrane cell hyperplasia, and by lymphoid aggregates. Synovitis contributes significantly to cartilage injury in rheumatoid and other inflammatory arthropathies. The role of synovial inflammation in the early stages of OA are less well understood, however synovitis is present at the clinical stage of OA. Cruciate-deficient mammal knee models, especially the Pond-Nuki model where the cruciate ligament is transected by a blind stab incision, produce intra-articular bleeding. Where hemostasis is observed and bleeding is carefully controlled, synovitis can be avoided. However, when a comparison is made between a group of mammals with synovitis and a group of mammals without synovitis, changes in articular cartilage from the two groups are indistinguishable.

As already mentioned, the activities of cytokines are an important part of the pathology of cartilage injury and loss. Cytokines are intercellular messengers which play an essential role in normal physiology, and with regard to articular cartilage, maintain its integrity by controlling the competing anabolic and catabolic processes which occur. The cytokines are released from cells and most often have multiple and overlapping activities. Cytokines are soluble glycoproteins which act nonenzymatically in picomolar to nanomolar concentrations to regulate host cell function. The release of the cytokines is prompted by specific signals, and the cytokines influence various functions in the cells which they target by means of affecting gene expression in those cells. Cytokines have a relatively short half-life and exert their influence within the immediate environment of the host cell (autocrine activity) or adjacent cells (paracrine activity) which they reach through the intracellular space. Cytokines may bind to receptors on their host cell surface or a neighboring cell surface, or within the host cell to an internal factor, or by direct cell-cell communication via membrane bound cytokines.

Cytokine homeostasis is maintained by its interaction with naturally occurring inhibitors. Receptor antagonists competitively bind to the cytokine binding-site preventing signal transduction, autoantibodies bind to the cytokine and neutralize it, and cytokine-binding proteins and soluble receptors remove the cytokine from the pool of active mediators. For example, the IL-1 receptor antagonist protein (IRAP) blocks IL-1 from binding to both of its receptors. Autoantibodies to IL-1α (sIL-1R) and insulin-like growth factor-binding proteins (IGF-BPs) exist, and they may serve to remove the cytokine ligands from the pool of active mediators, or may prevent proteolytic destruction of the cytokines, or may act as transport proteins for the cytokines. Cytokines may even oppose the activity of other cytokines. For example, IL-1 activity is reduced in the presence of transforming growth factor beta (TGFβ) and IGF-1.

Disruption of the intricate balance among the above-described cytokines and their regulators may precipitate or contribute to pathologic changes in the joint. In such a joint the articular cartilage protects the subchondral bone from mechanical stresses. The cartilage is a highly specialized connective tissue comprising water, collagen and proteoglycans which together create a unique fiber-reinforced water gel which is stiff but resilient and has considerable shock-absorbing capacity. The extracellular matrix of the cartilage is produced by the chondrocytes which are highly active, and the integrity of this matrix is maintained by an equilibrium between the actions of the catabolic cytokines IL-1α, β and TNFα and the anabolic cytokines IGF and TGFβ. IL-1α, β and TNFα act by inducing the production of specific matrix degrading metalloproteases, while IGF and TGFβ act as growth factors by inducing the production of the macromolecular building blocks of cartilage, collagen and the proteoglycans. Other cytokines and their inhibitors, as well as tissue inhibitors of metalloprotease (TIMP), also influence this equilibrium, referred to as matrix homeostasis.

The term "metalloprotease" as used herein is intended to refer to the matrix metalloproteases (MMPs), especially including those in this family of enzymes which usually exhibit elevated concentrations during articular cartilage degeneration, i.e., the stromelysins, the collagenases, and the gelatinases. Collagenase is generally responsible for the degradation of native collagen; stromelysin is generally responsible for the degradation of the proteoglycans; and gelatinase is generally responsible for the degradation of denatured collagen. An enzyme with MMP properties, aggrecanase, is also included within this term, since it is responsible for the proteolysis of cartilage proteoglycan aggregates which are present during the early stages of cartilage degeneration. The three collagenases present in articular cartilage during the early stages of degeneration are collagenase-1 (MMP-1), collagenase-2 (MMP-8), and collagenase-3 (MMP-13). Of the three stromelysins, stromelysin-1 (MMP-3), stromelysin-2 (MMP-10), and stromelysin-3 (MMP-11), only stromelysin-1 appears in articular cartilage during the early stages of its degeneration.

The early stages of the pathologic changes leading to cartilage injury and loss involve attempted repair through increased synthesis of matrix macromolecules. The makeup of the repair cartilage is deficient however, due to altered composition and distribution of the glycosaminoglycan component and a change in its capacity to aggregate with the hyaluronic acid component. Particles released during these pathologic changes may also lead to inflammatory changes in the synovial membrane. However, despite this ongoing pathology, the initial stages of cartilage injury and loss may be asymptomatic with relatively little pain. Accordingly, an appropriate objective is to identify those extracellular matrix components and cytokines for which measurable changes may be identified which profile a mammal subject in the early stages of cartilage injury and loss before focal cartilage loss can be identified radiographically. Meeting this objective will permit diagnostic classification of mammals which are candidates for early pharmacological intervention before significant cartilage degeneration occurs.

IL-1, which occurs as IL-1α and IL-1β, is a catabolic cytokine which mediates articular cartilage injury and loss in mammal joints. It acts by suppressing the synthesis of type II collagen found in articular cartilage while promoting the synthesis of type I collagen characteristic of fibroblasts; by inducing the production of enzymes involved in matrix degradation; and by suppressing the ability of chondrocytes to synthesize new proteoglycans. The number of IL-1 receptors on the surface of chondrocytes in articular cartilage in the early stages of degeneration which must be occupied in order to elicit catabolic enzyme production is only one-fourth as great as that required normally (1% vs. 4%). IL-1 and its modulator IRAP are produced in an autocrine and paracrine fashion by the same synovial macrophages, and IRAP production may be increased in the presence of granulocyte macrophage colony-stimulating factor (GM-CSF). However, there is a significant disparity between IL-1 and IRAP potency, with approximately 130-fold more IRAP being required to abolish the effects of IL-1, as measured in chondrocytes and cartilage explants. Any imbalance between IL-1 and IRAP will further exacerbate the degeneration of articular cartilage.

Consequently, it is also an appropriate objective to measure levels of IL-1 and IRAP and their ratios in mammals in the early stages of articular cartilage degeneration, and the same values in mammals not so afflicted so that measurable changes may be identified which profile a mammal subject in the early stages of cartilage injury and loss before focal cartilage loss can be identified radiographically. These results provide diagnostic classification of mammals which are candidates for early pharmacological intervention before significant cartilage degeneration occurs. Furthermore, the proportion of IL-1α and IL-1β-secreting macrophages occurring in the synovial fluid and synovial tissue of a joint in the early stages of articular cartilage degeneration can be detected and is significantly greater than the proportion of similar cells isolated from synovial fluid and synovial tissue from normal joints, i.e., joints which are not in the early stages of articular cartilage degeneration. Here again, these results provide diagnostic classification of mammals which are candidates for early pharmacological intervention before significant cartilage degeneration occurs.

Further still, changes in subchondral bone occur before gross alterations in the articular cartilage become apparent because cytokines responsible for initiating and maintaining the inflammatory process gain access to the lower layers of cartilage through microcracks across the calcified zone. The metabolism of the chondrocytes involved is adversely affected, and in addition the chondrocytes in the middle zone of the articular cartilage produce many cytokines, including those responsible for initiating and maintaining the inflammatory process. These chondrocytes, acting in an autocrine fashion, thus contribute to the destruction of their own extracellular matrix. The increased water content of the articular cartilage also facilitates this process by increasing diffusion of the inflammatory cytokines throughout the matrix. It is, consequently, an appropriate objective to measure levels of various inflammatory cytokines produced by chondrocytes, synovial cells, and/or subchondral osteocytes in mammals, especially canines during the process of articular cartilage degeneration, and the same values in mammals not so afflicted so that measurable changes may be identified which profile a mammal subject in the early stages of cartilage injury and loss before focal cartilage loss can be identified radiographically. These results provide diagnostic classification of mammals which are candidates for early pharmacological intervention before significant cartilage degeneration occurs.

Tumor necrosis factor alpha (TNFα) has only one-tenth the potency of IL-1 with regard to the degeneration of articular cartilage, but its concentration in synovial fluid significantly increases in the knee joints of mammals, especially with sectioned cruciate ligaments compared to the opposite, unoperated knee. There is also enhanced expression of p55 TNF receptors (TNF-R) on chondrocytes isolated from articular cartilage present in such knee joints. Accordingly, since TNFA plays a role in the pathologic changes which take place in the early stages of cartilage injury and loss, it is likewise an appropriate objective to measure levels of TNFα and TNF-R in the joints of mammals in the early stages of articular cartilage degeneration, and the same values in mammals not so afflicted so that measurable changes may be identified which profile a mammal subject in the early stages of cartilage injury and loss before focal cartilage loss can be identified radiographically. These results provide diagnostic classification of mammals which are candidates for early pharmacological intervention before significant cartilage degeneration occurs.

Interleukin-6 (IL-6) is a multifunctional cytokine, but plays an inflammatory role and is found in elevated levels in joints and synovial fluid from damaged as compared to control limbs. IL-6 is also responsible for enhanced expression of TNF-R on chondrocytes and increased proteoglycan production by chondrocytes, as well as induction of glycosaminoglycan release. Measurement of IL-6 levels in joints, synovial fluid and chondrocytes of mammal joints in the early stages of articular cartilage injury and loss, compared to control, can be used as a diagnostic tool for identifying mammals that are appropriate candidates for pharmacological treatment, before any focal cartilage loss is evident from radiographic examination.

Leukemia inhibitory factor (LIF) is produced by monocytes, granulocytes, T cells, fibroblasts, and other cell types associated with inflammatory conditions. Synoviocytes and chondrocytes synthesize and secrete LIF in the presence of IL-1β and TNFα. Thus, measurement of comparative increases in levels of LIF can be used diagnostically to select mammal candidates for pharmacologic treatment of the early stages of articular cartilage injury and loss.

The degeneration, injury and loss of articular cartilage in mammals is caused by an imbalance between the cytokines that drive the above-described catabolic processes and those cytokines which are responsible for maintaining the synthetic and proliferative responses of the chondrocytes in the cartilage. Insulin-like growth factor (IGF-1), transforming growth factor beta (TGFβ), platelet-derived growth factor (PDGF), and fibroblast growth factor, e.g., basic fibroblast growth factor (bFGF), are all mitogenic with respect to the chondrocytes and stimulate matrix synthesis in articular cartilage.

Insulin-like growth factor (IGF) exists as types I and II, and IGF-I is a potent mediator of cartilage synthesis. Furthermore, it reduces degradation and promotes synthesis of proteoglycans even in the presence of IL-1β and TNFα. Serum levels of IGF-1 are maintained by high-affinity binding proteins (IGF-BPs) and IGF-1 is important in both bone and cartilage turnover. Levels of IGF-1 compared to control permit diagnostic evaluation of mammal candidates for early pharmacologic treatment of articular cartilage degeneration.

Transforming growth factor (TGFβ) is produced by chondrocytes and is a powerful mitogen for the turnover of both cartilage and bone. Further, it stimulates the synthesis of matrix and has anti-inflammatory activity. It also inhibits the degradation of the matrix by stimulating protease inhibitor production, and blocking collagenase and metalloprotease release. Further still, it promotes cartilage repair by stimulating production of collagen, fibronectin, inhibitors of plasminogen activators, and tissue inhibitors of metalloproteases (TIMP) by various cells in the mammal joint. Synovial fluid levels of TGFβ are low in the joints of mammals in the early stages of articular cartilage injury and loss. Consequently, levels of TGFβ compared to control permit diagnostic evaluation of mammal candidates for early pharmacologic treatment of articular cartilage degeneration.

With the progressive degeneration, i.e., catabolism of the articular cartilage in the mammal joint, a number of metabolites are produced which are useful as markers of the cartilage degeneration, both as to its occurrence and as to its advance. For example, degradation of cartilage by IL-1α and IL-1β or TNFα releases glycosaminoglycans (GAGS), which can be measured in the synovial fluid of a mammal being tested. Furthermore, GAG levels change after treatment so that it is possible to monitor the course of pharmacologic intervention, using synovial fluid GAG levels as a marker of articular cartilage turnover.

Since the degradation of articular cartilage involves collagen as well as the other cartilage components, several collagen products serve as markers of cartilage degradation in mammal, especially canine articular cartilage injury and loss. Type-II specific collagen breakdown products, e.g., 20–30 amino acid neoepitopes, can be identified in body fluids such as synovial fluid, plasma, serum or urine. The presence of neoepitopes in these body fluids may be used as indicators of OA onset and progression.

Keratan sulfate is a particular GAG which has an epitope, 5D4, whose levels in synovial fluid can be used as a marker of early articular cartilage injury and loss. Conversely, levels of chondroitin sulfate, another particular GAG, expressed as a number of epitopes, is associated with anabolic events in the articular cartilage of mammals in the early stages of cartilage injury and loss. Levels of these epitopes in synovial fluid, particularly 3B3, 7D4 and 846, can be determined by specific monoclonal antibodies which recognize them. The 3B3 epitope is expressed on chondroitin sulfate chains of cartilage during repair and the remodeling of the extracellular matrix, and consequently its levels in synovial fluid correlate inversely with those of the above-mentioned 5D4. The expression of 3B3 in newly synthesized PGs in the superficial and upper middle layer of the articular cartilage mean that 3B3 is associated with early changes in the articular cartilage of mammals in the early stages of cartilage degeneration. Accordingly, the determination of 3B3 levels in the synovial fluid of test mammals and comparison of these levels with control values permits the creation of a diagnostic profile of a mammal that is an appropriate candidate for early pharmacologic treatment.

Further markers of cartilage anabolic activity are the propeptides of type II procollagen (PIIP). Type II is the major collagen of articular cartilage and it is produced by the chondrocytes as procollagen. During the process of collagen fibril formation, the noncollagenous aminopropeptide and carboxypropeptide are cleaved and released into body fluids, where they can be measured as reflection of anabolic activity in the articular cartilage. Levels of carboxy-PIIP will be raised and its synovial fluid levels correlate with radiographic evidence of changes in the cartilage. Accordingly, measurement of carboxy-PIIP levels in synovial fluid and comparison with controls permits identification of mammal candidates for early pharmacologic treatment.

An imbalance in the stromelysin/TIMP ratio in the articular cartilage and joint fluids of mammals in the early stages of articular cartilage degeneration is also useful in identifying such mammals. Altered joint loading following injury causes the production of excess stromelysin, an enzyme produced by chondrocytes and synoviocytes under the influence of IL-1. The concentrations of stromelysin are also higher in fibrillated cartilage than they are in cartilage more distal from the lesion involved. The increased levels of stromelysin may occur for only a fairly short period of time, but where the damage to the joint transcends the tidemark zone of the articular cartilage, and reaches into the subchondral bone, there is a substantial likelihood of subsequent articular cartilage degeneration, usually preceded by a stiffening of the subchondral bone.

Further, in the cruciate-deficient mammal model used in detecting the early stages of articular cartilage degeneration, there is an increased number of cells involved in the synthesis of stromelysin, IL-1α, IL-1β, and three oncogene proteins, c-MYC, c-FOS, and c-JUN. In the synovium these are found mainly in the superficial synovial lining cells, while in the cartilage the cells are the chondrocytes on the superficial and middle layers and the cells in the fibrillated areas of the tibial plateau. Further, stromelysin and IL-1 diffuse into the cartilage matrix of the tibial plateau. Stromelysin, which degrades components of connective tissue including proteoglycans and type IX collagen, is actively synthesized in the synovium of mammals in the early stages of articular cartilage degeneration, and is the primary proteolytic enzyme involved in the cartilage destruction. Increased levels of stromelysin mRNA are detectable in the synovia of such mammals, as are increased levels of collagenase mRNA. Increased levels of both isoforms of IL-1, but especially IL-1β, stimulate the increased synthesis of stromelysin by enhancing synovial fibroblast induction of stromelysin and collagenase gene expression. At the same time, IL-1 does not induce mRNA of tissue inhibitor of metalloprotease (TIMP) and the levels of this inhibitor remain unchanged while the detectable levels of metalloproteases in the synovium are dramatically increased.

The metalloproteases are secreted by chondrocytes as proenzymes which must be activated before degradation of extracellular matrix macromolecules can take place. Activation involves an enzymatic cascade in which serine proteases including the plasminogen activator/plasmin system play a key role.

The integrity of the articular cartilage in a mammal joint depends upon the adequacy of the support which it receives from the bony bed which it covers, i.e., the structural properties of the underlying subchondral bone. Alterations in this bony bed precede degradative changes in the articular cartilage. These alterations include increased stiffening of the subchondral bone, accompanied by loss of shock-absorbing capacity. These subchondral bone changes are caused by inappropriate repair of trabecular microfractures which result, in turn, from excessive loading of the joint. Trabecular thickening of the subchondral bone is part of a bone alteration leading to increased bone mineral density and/or volume in affected joints, which in turn is caused by a bone cell defect in the osteoblasts, resulting in altered phenotypic characteristics in these osteoblast-like cells of the subchondral bone.

These alterations in subchondral bone density are not only evidence of an imbalance in the bone remodeling process, but also are a key ingredient in eventual focal cartilage loss. Bone sclerosis is also due to dysregulation of this bone remodeling process. Further, site-related differences in osteoblast metabolism occur which lead to the production of different cartilage-degrading molecules. These changes in osteoblast metabolites in turn lead to corresponding changes in chondrocyte metabolism, rendering them more susceptible to cytokine-induced activity of the types above-described. This osteoblastic anomaly and differentiated phenotype is characterized by divergent production levels of osteocalcin, alkaline phosphatase, cAMP responsive to hormone challenge, urokinase plasminogen activator (uPA), and insulin-like growth factor 1 (IGF-1).

Further evidence of subchondral bone activity involvement in eventual articular cartilage degeneration is joint space narrowing which may be measured by bone scintigraphy. These changes in subchondral bone activity are accompanied by corresponding changes in specific bone cell metabolites, e.g., osteocalcin. Osteocalcin is a vitamin K-dependent, calcium binding bone protein which is the most abundant noncollagen protein in bone. Increased levels of osteocalcin are a marker of bone turnover in various disease states, including particularly the early stages of articular cartilage degeneration. Body fluid, especially synovial fluid levels of osteocalcin directly correlate to subchondral bone changes as measured by scintigraphy.

In addition to markers of subchondral bone activity as indicators of the early stages of articular cartilage degeneration in mammals, metabolites from cartilage and synovium activity are also useful as markers which indicate the early stages of such cartilage degeneration. For example, detection of increased serum levels of cartilage oligomeric matrix protein serves as a marker of cartilage turnover. Similarly, detection of high levels of hyaluronate in body fluids, especially serum serves as a marker of synovial inflammation. In both cases, the increased body fluid, especially serum levels of these metabolite markers indicate the early stages of articular cartilage degeneration.

The expression "body fluid" as used herein in intended to include all of those accessible body fluids usable as clinical specimens which may contain a compound being tested for in sufficient concentration in said fluid to be within the limits of detection of the test device or assay being used. Body fluids will thus include whole blood, serum, plasma, urine, cerebrospinal fluid, synovial fluid, and interstitial and other extracellular fluids.

As with all sensitive immunochemical and other biological assays of the type above-described, significant care must be exercised in the collection and storage of the fluids to be tested. Steps should be taken to avoid proteolysis of the compounds to be tested for in said fluids, and freezing is usually warranted unless the test involved can be carried out within a short period of time. It is usually preferable to use synovial fluid rather than serum because of the likelihood that there will be greater concentrations of the compounds being tested for in the synovial fluid. On the other hand, increased levels of viscosity in synovial fluids pose problems in immunoassay systems which must be addressed by the artisan. Finally, as will be clear from the above-description, it is preferable to conduct longitudinal studies of a selection of cytokines and markers as well as their respective inhibitors and binding proteins in order to obtain the most accurate profile possible in determining whether a mammal subject is in the early stages of articular cartilage degeneration, and is therefore a candidate for pharmacologic intervention.

As used herein, the term "mammal(s)" denotes any mammal, of which there are a large number of different breeds. While laboratory determinations of biological activity may have been carried out using a particular breed, it is contemplated that the chondroprotective compounds of the present invention will be found to be useful for treating and preventing the early stages of articular cartilage degeneration in any of these numerous breeds.

The term "chondroprotective" as used herein refers to the biological activity of the carprofen and derivative compounds used in the methods and compositions of the present invention which permits said compounds to ameliorate, diminish, actively treat, reverse or prevent any injury, damage or loss of articular cartilage or subchondral bone subsequent to the early stages of degeneration in said articular cartilage or subchondral bone. Optimally, the chondroprotective compound will arrest or cause a reversal of the disease process whereby injury, damage or loss of the articular cartilage or subchondral bone takes place. However, said chondroprotective compound may provide less than such optimal results and still be within the scope of the present invention. Even in those instances where the chondroprotective compound administered fails to provide more than ameliorative results, the method of treatment is still contemplated to be within the scope of the present invention.

Variation in results arises from a number of factors, including the particular variety of mammal as well as the specific individual mammal being administered said chondroprotective compound. The stage to which the disease has advanced, i.e., the extent of injury, damage or loss to the articular cartilage or the subchondral bone which has already taken place, will affect the results. The more the disease has progressed, the more difficult it will become to arrest or reverse the disease process. The particular chondroprotective compound which is selected for administration can also have an impact on the results, as can the dose of said compound administered, the type and site of administration thereof, and the particular dosage form which is used.

The expression "treating or preventing" as used herein with reference to the administration of the chondroprotective compounds of the present invention, is intended to refer to both the therapeutic objective of said administration as well as the therapeutic results actually achieved by said administration. As above-discussed, the extent of therapy accomplished by administration of the chondroprotective compounds may range from an amelioration to a significant diminishing of the course of the disease, and beyond to active treatment of the disease, including a reversal of the disease process. The higher degrees of therapeutic effectiveness result in the prevention of any injury, damage or loss of articular cartilage or subchondral bone subsequent to the early stages of degeneration in said articular cartilage or subchondral bone.

The expression "the early stages of degeneration in articular cartilage or subchondral bone" is intended to mean the very beginning of the initial pathologic changes in the articular cartilage or subchondral bone which define and are the result of a disease process. Said pathologic changes include changes in the composition, form and density of the articular cartilage from that present before the onset of said disease process, which result in a degradation of the beneficial properties of said articular cartilage including strength, resilience, elasticity, conformational integrity and stability, viability, and the ability to successfully resist various kinds of mechanical stress, especially the ability to absorb mechanical shocks. These pathologic changes in composition especially include changes in the type and amount of glycosaminoglycans and collagen fibers present in the articular cartilage.

Pathologic changes in the subchondral bone include sclerosis thereof, increasing density with decreasing resilience and elasticity thereof, and a diminishing ability to successfully resist various kinds of mechanical stress, especially the ability to absorb mechanical shocks. These pathologic changes especially include improper repair of trabecular microfractures with trabecular thickening, and pathogenic changes in osteoblastic metabolite production and differentiated phenotype.

In its broadest aspects, the gist of the present invention is the surprising discovery that a small genus of chondroprotective agents, of which carprofen, 6-chloro-α-methyl-9H-carbazole-2-acetic acid, is the most preferred species, when administered to a mammal subject identified as being in the early stages of articular cartilage degeneration which will eventually result in injury, damage or loss of articular cartilage or subchondral bone in any involved joints thereof, will ameliorate, diminish, actively treat, reverse or prevent such injury, damage or loss. This ability of the chondroprotective agents of the present invention to reverse the disease process which ultimately leads to articular cartilage and subchondral bone destruction and loss has far-reaching implications for the safe and effective treatment of mammals which are in the early stages of articular cartilage and subchondral bone degeneration.

Accordingly, the present invention provides a method of treating or preventing degeneration or destruction of articular cartilage or subchondral bone in the joints of a mammal in need of such treatment, comprising (1) establishing the status of said mammal as presently or prospectively being in said early stages and thus in need of such treatment; and thereupon (2) administering to said member an amount therapeutically effective for treating or preventing said degeneration or destruction of articular cartilage or subchondral bone, of a chondroprotective compound of Formula (I):

Formula (I)

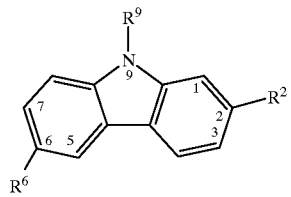

wherein:

$R^2$ is 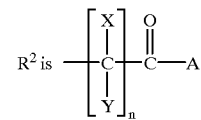

where A is hydroxy, $(C_1-C_4)$alkoxy, amino, hydroxy-amino, mono-$(C_1-C_2)$alkylamino, di-$(C_1-C_2)$alkylamino; X and Y are independently H or $(C_1-C_2)$alkyl; and n is 1 or 2;

$R^6$ is halogen, $(C_1-C_3)$alkyl, trifluoromethyl, or nitro;

$R^9$ is H; $(C_1-C_2)$alkyl; phenyl or phenyl-$(C_1-C_2)$alkyl, where phenyl is optionally mono-substituted by fluoro or chloro; —C(=O)—R, where R is $(C_1-C_2)$alkyl or phenyl, optionally mono-substituted by fluoro or chloro; or —C(=O)—O—$R^1$, where $R^1$ is $(C_1-C_2)$alkyl;

where X and Y are different, the (−)(R) and (+)(S) enantiomers thereof; and all pharmaceutically acceptable salt forms, prodrugs and metabolites thereof which are therapeutically active for treating or preventing degeneration or destruction of articular cartilage or subchondral bone. Where the inhibitor of Formula (I) exists as (−)(R) and (+)(S) enantiomers, in accordance with the present invention there is provided the (+)(S) enantiomer alone, or where both enantiomers are present together, there is provided a racemic or a non-racemic mixture thereof.

Carprofen and the genus of carprofen derivatives utilized in the methods and compositions of the present invention may be prepared in accordance with methods of synthesis well known to the organic chemist of ordinary skill. For example, compounds of Formula (I) where $R^6$ is halogen, $(C_1-C_3)$alkyl, trifluoromethyl, or nitro; and where $R^9$ is H or methyl; may be prepared by reacting (1) a phenylhydrazine in which the phenyl portion has the desired $R^6$ substitution and the α-nitrogen of the hydrazine has the desired $R^9$ substitution; with (2) a cyclohexanone having the desired $R^2$ substitution. The resulting 1,2,3,4-tetrahydrocarbazole is then aromatized to produce the desired carbazole of Formula (I). The aromatization may be carried out using (1) an aromatizing agent, e.g., p-chloranil, o-chloranil, 2,3-dichloro-5,6-dicyanobenzoquinone (DDQ), sulfur, palladium on carbon, or lead oxide; in the presence of (2) a solvent such as xylene, benzene, toluene, quinoline, dimethylsulfoxide (DMSO), and dimethylformamide (DMF); (3) at a temperature in the range from room temperature to reflux of the reaction mixture, preferably the latter.

Compounds of Formula (I) which are acids, i.e., where A is hydroxy, and salts of such acids with bases, can be converted to amides of Formula (I) where A is amino, hydroxyamino, mono-$(C_1-C_2)$alkylamino, and di-$(C_1-C_2)$alkylamino; by (1) forming the corresponding acid chloride by treatment with phosphorus pentachloride ($PCl_5$); followed by (2) reaction with the appropriate amine reactant to form the desired amide, carried out in the presence of an equivalent of pyridine or triethylamine to serve as the base for the proton transfer step and thereby remove the $H^+Cl^-$ which is formed. The same acid chlorides which are formed in step (1) can be reacted with the appropriate alkanol to provide the esters of Formula (I) where A Is $(C_1-C_4)$alkoxy. This reaction is also desirably carried out in the presence of a base such as pyridine which can neutralize the $H^+Cl^-$ being formed so that it does not interfere with any acid sensitive alkanol reactant.

The above-described synthetic approaches to preparation of the carprofen genus of compounds utilized in the methods and compositions of the present invention are described in detail in U.S. Pat. No. 3,896,145, which is incorporated herein by reference in its entirety.

When "X" and "Y" are different in the definition of the "$R^2$" substituent, then a chiral (asymmetric) carbon atom exists. A racemic mixture of (R)- and (S)-enantiomers results when there is a 50:50 mixture of the two enantiomers. In accordance with the present invention the (S)-enantiomer of the carprofen genus of compounds of Formula (I) having a chiral carbon is the enantiomer which possesses the highest level of activity in treating or preventing degeneration or destruction of the articular cartilage or subchondral bone of a mammal subject identified as being in the early stages of articular cartilage degeneration which eventually results in injury or loss of cartilage or subchondral bone in any involved joints thereof.

One especially preferred embodiment of the present invention is to use only the (S)-enantiomer of carprofen, 6-chloro-α-methyl-9H-carbazole-2-acetic acid, as the active ingredient or treating agent in the methods and compositions of the present invention. However, other embodiments are contemplated to be within the scope of this preferred genus of the present invention as well. For example, non-racemic mixtures of the (R)- and (S)-enantiomers can be used, and in that event the (S)-enantiomer is present in amount of at least 85%, preferably at least 90%, more preferably at least 95%, and most preferably at least 99%. Since the (R)- and (S)-enantiomers are identical in molecular weight, density, etc., it is unnecessary to state any basis for the above-recited percentages. In other words, they could be percentages by weight, volume, chemical equivalency, etc. The reason for including the above-indicated amounts of the (R)-enantiomer may be as simple as the practicalities of not being required to remove absolutely every last trace of the (R)-enantiomer from the racemic mixture. There can also be reasons for doing so which relate to beneficial overall biological properties.

It will also be appreciated by those in the art that the ranges of dosage amounts recited elsewhere herein for the genus of carprofen compounds are being described with respect to a 50:50 racemic mixture of enantiomers, where a chiral compound is involved. This has been done largely as a matter of convenience. Where the active ingredient being used as a therapeutic agent comprises a mixture of enantiomers different from a 50:50 mixture, or where the therapeutic agent comprises substantially 100% of the (+)(S) or (−)(R) enantiomer alone, the person of ordinary skill in this art will be able to calculate the actual amount of dosage required in a very straightforward manner, simply by multiplying the dosage amounts recited by a factor which reflects the ratio of the amount of enantiomer being used to the amount present for the recited dosage based on a 50:50 mixture of the enantiomers. Accordingly, where the recited dosage is 4 mg/kg/day for the 50:50 racemic mixture, the corresponding dosage amount when substantially 100% of (+)(S) enantiomer is used one-half of the recited amount, i.e., 2 mg/kg/day.

Since the pharmaceutical compositions of the present invention containing a member of the preferred genus of carprofen compounds contemplate the use of racemic mixtures containing 50% of (S)-enantiomer, as well as non-racemic mixtures of about 99% or less of the (S)-enantiomer along with less than 50% of the (R)-enantiomer, resolution of racemates of the carprofen genus of compounds of Formula (I) having a chiral carbon into the optically active isomers must be carried out. This can be readily accomplished using known procedures and techniques in the art. For example, some racemic mixtures can be precipitated as eutectics after which they can be separated. However, it is usually preferred to use chemical procedures for resolution, in accordance with which diastereomers are formed from the racemic mixture with an optically active resolving agent. For example, an optically active base, e.g., D-α-methylbenzylamine, which can be reacted with the carboxyl group. The diastereomers thus formed are then separated by selective crystallization and converted to the corresponding optical isomer.

Included within the scope of the present invention are all of the chondroprotective, therapeutically active, and pharmaceutically acceptable salt forms, prodrugs and metabolites of the carprofen genus of compounds used in the present invention. This especially includes acid addition salts thereof, where "A" is defined as anything other than "hydroxy", formed by treating the compounds of Formula (I) with pharmaceutically acceptable organic and inorganic acids, e.g., hydrohalides such as hydrochloride, hydrobromide, hydroiodide; other mineral acids and their corresponding salts such as sulfate, nitrate, phosphate, etc.; and alkyl- and mono-arylsulfonates such as ethanesulfonate, toluenesulfonate, and benzenesulfonate; and other organic acids and their corresponding salts such as acetate, tartrate, maleate, succinate, citrate, benzoate, salicylate, ascorbate, etc.

Where "A" is defined as "hydroxy" in the carprofen genus of compounds used in the present invention, salts thereof may be formed by treatment with pharmaceutically acceptable bases. Examples of such bases are alkali metal hydroxides including potassium hydroxide, sodium hydroxide, and lithium hydroxide; alkaline earth metal hydroxides such as barium hydroxide and calcium hydroxide; alkali metal alkoxides, e.g., potassium ethanolate and sodium propanolate; and various organic bases such as piperidine, diethanolamine, and N-methylglutamine. Also included are the aluminum salts of the compounds of Formula (I).

In addition to the use of the various above-described salt forms of the compounds of Formula (I), there is included within the scope of the present invention the use as active ingredients of all chondroprotective, therapeutically active, and pharmaceutically acceptable prodrugs and metabolites of the above-recited compounds. In particular, this includes those derivatives where $R^9$ is defined as $(C_1-C_2)$alkyl, especially methyl; phenyl or phenyl-$(C_1-C_2)$alkyl, especially benzyl, where phenyl is optionally mono-substituted by fluoro or chloro, especially 4-fluoro-phenyl; —C(=O)—R, where R is $(C_1-C_2)$alkyl or phenyl, especially acetyl and benzoyl, where phenyl is optionally mono-substituted by fluoro or chloro; or —C(=O)—O—$R^1$, where $R^1$ is $(C_1-C_2)$alkyl, especially acetyloxy. These N-moieties are readily cleaved during metabolism of the compound of Formula (I), making these particular derivatives desirable prodrugs.

When the compounds of Formula (I), or their enantiomers or salts, are to be used as active ingredients in the methods and compositions of the present invention, they can be incorporated into standard pharmaceutical dosage forms. For example, they are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elixirs. Pharmaceutical excipients and adjuvants which can be added include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers. Particular dosage forms which have been used with success include a 5% mixed-micelle solution of carprofen for intravenous injection, a 3% palatable paste, and oral tablets in 25 mg, 75 mg, and 100 mg dosages.

In the methods and compositions of the present invention, especially those wherein the inhibitor comprises 6-chloro-α-methyl-9H-carbazole-2-acetic acid and both resulting enantiomers are present together, it is a preferred embodiment to use a non-racemic mixture. Particularly, in such preferred non-racemic mixtures, it is desirable to have the (+)(S) enantiomer present in amount of at least 85%, preferably at least 90%, more preferably at least 95%, and most preferably at least 99%. Thus, in such non-racemic mixtures the (+)(S) enantiomer will be the predominant component, because it is significantly more potent than the (−)(R) enantiomer in providing chondroprotection. The correspondingly smaller amounts of the (−)(R) enantiomer, ie., less than 15%, less than 10% and less than 5%, respectively, are optionally included where a balance of chondroprotective properties is deemed desirable. Where the amount of (−)(R) enantiomer present is less than 5% and less than 1%, the reason for the inclusion will usually reflect the practicalities of the method used to resolve the enantiomers. Where this method is time consuming or demanding of resources, it will often be desirable, from a practical standpoint, to simply allow this smaller proportion of the (−)(R) enantiomer to be carried over into the final, non-racemic mixture final product.

The chondroprotective compounds of Formula (I) of the present invention may be administered systemically to a mammal to be treated as a pharmaceutical composition in suitable liquid form by injection or infusion. There are a number of sites and organ systems in the body of the mammal which will allow the properly formulated pharmaceutical composition, once injected or infused, to permeate the entire body and all of the organ system of the mammal being treated. An injection is a single dose of the pharmaceutical composition forced, usually by a syringe, into the tissue involved. The most common types of injections are intramuscular, intravenous, and subcutaneous. By contrast, an infusion is the gradual introduction of the pharmaceutical composition into the tissue involved. The most common type of infusion is intravenous. Other types of injection or infusion comprise intraarterial, intra- or transdermal (including subcutaneous), or intraspinal especially intrathecal. In these liquid pharmaceutical compositions, the chondroprotective compound may be contained in solution as the solute. This is the most common and most preferred type of such composition, but requires a compound of Formula (I) in a salt form that has reasonably good aqueous solubility. Water (or saline) is by far the most preferred solvent for such compositions. Occasionally supersaturated solutions may be utilized, but these present stability problems that make them impractical for use on an everyday basis.

If it is not possible to obtain a form of some compound of Formula (I) that has the requisite degree of aqueous solubility, as may sometimes occur, it is within the skill of the artisan to prepare an emulsion, which is a dispersion of small globules of one liquid, the discontinuous or internal phase, throughout a second liquid, the continuous or external phase, with which it is immiscible. The two liquids are maintained in an emulsified state by the use of emulsifiers which are pharmaceutically acceptable. Thus, if the chondroprotective compound of Formula (I) is a water-insoluble oil, it can be administered in an emulsion of which it is the discontinuous phase. Also where the inhibitor is water-insoluble but can be dissolved in a solvent which is immiscible with water, an emulsion can be used. While the compound of Formula (I) would most commonly be used as the discontinuous or internal phase of what is referred to as an oil-in-water emulsion, it could also be used as the discontinuous or internal phase of an inverse emulsion, which is commonly referred to as a water-in-oil emulsion. In this instance the compound of Formula (I) is soluble in water and could be administered as a simple aqueous solution.

However, inverse emulsions invert upon injection or infusion into an aqueous medium such as the blood, and offer the advantage of providing a more rapid and efficient dispersion of said compound into that aqueous medium than can be obtained using an aqueous solution. Inverse emulsions are prepared by using suitable, pharmaceutically acceptable emulsifying agents well known in the art. Where the chondroprotective compound of Formula (I) has limited water solubility, it may also be administered as a suspended solid in colloidal or microparticulate form in a suspension prepared using suitable, pharmaceutically acceptable suspending agents. The suspended solids containing said compound may also be formulated as delayed-, sustained-, and/or controlled-release compositions.

While systemic administration will most frequently be carried out by injection or infusion of a liquid, there are many situations in which it will be advantageous or even necessary to deliver the chondroprotective compound of Formula (I) as a solid. Systemic administration of solids is carried out by instillation of a pharmaceutical composition in suitable solid form containing said compound. Instillation of said compound may entail installing a solid implant composition into suitable body tissues or cavities. The implant may comprise a matrix of bio-compatible and bio-erodible materials in which particles of a solid chondroprotective compound of Formula (I) are dispersed, or in which, possibly, globules or isolated cells of a liquid chondroprotective compound of Formula (I) are entrapped. Desirably, the matrix will be broken down and completely absorbed by the body. The composition of the matrix is also preferably selected to provide controlled-, sustained-, and/or delayed release of said compound of Formula (I) over extended periods of time, even as much as several months.

A substantial number of the dosage forms described herein may be formulated so as to provide controlled-, sustained-, and/or delayed release of the active ingredient from said dosage form. In an especially preferred aspect of the pharmaceutical compositions of the present invention which provide delayed-, sustained-, and/or controlled-release of the chondroprotective compound of Formula (I) active ingredient, there is included all such orally administered dosage forms which result in a plasma concentration of said compound of at least 10 $\mu$g/mL for at least 4 hrs; preferably for at least 8 hrs; more preferably for at least 12 hrs; more preferably still for at least 16 hrs; even more preferably still for at least 20 hrs; and most preferably for about 24 hrs. Preferably, there is included the above-described dosage forms which result in a plasma concentration of said inhibitor of at least 15 $\mu$g/mL for at least 4 hrs, preferably for at least 8 hrs, more preferably for at least 12 hrs, still more preferably for at least 20 hrs, and most preferably for about 24 hrs. More preferably, there is included the above-described dosage forms which result in a plasma concentration of said inhibitor of at least 20 $\mu$g/mL for at least 4 hrs, preferably for at least 8 hrs, more preferably for at least 12 hrs, still more preferably for at least 20 hrs, and most preferably for about 24 hrs.

Accordingly, a useful controlled release dosage form of carprofen in accordance with the present invention is one which maintains a carprofen plasma level greater than 2 $\mu$g/mL for most of the day after a single oral dose at 2 mg/lb. Preferred oral controlled release dosage forms of carprofen in accordance with the present invention are ones which maintain a plasma carprofen concentration greater than 10 $\mu$g/mL for a period of time greater than that for which an immediate release dosage form of carprofen maintains a comparable plasma level, when said immediate release dosage form and controlled release dosage form are administered at the same dose, e.g. 2, 1.8, 1.6, or 1.4 mg/lb. For instance, preferred 2 mg/lb oral controlled release dosage forms of this invention maintain a plasma carprofen concentration greater than 10 $\mu$g/mL for greater than 10.5 hrs.

Immediate release carprofen dosage forms containing doses of 1.8, 1.6, and 1.4 mg/lb maintain a plasma carprofen concentration above 10 $\mu$g/mL for 9.5 hrs, 8.5 hrs, and 7.5 hrs, respectively. Preferred 1.8 mg/lb oral controlled release carprofen dosage forms maintain a plasma carprofen concentration above 10 $\mu$g/mL for greater than 9.5 hrs. Likewise, the threshold durations for 1.6 mg/lb and 1.4 mg/lb doses are 8.5 hrs and 7.5 hrs, respectively. The performance characteristics for preferred oral controlled release carprofen dosage forms at doses higher than 2 mg/lb or less than 1.4 mg/lb can be similarly calculated, assuming linear pharmacokinetics. More preferred oral controlled release carprofen dosage forms are those which maintain a plasma carprofen concentration greater than 10 $\mu$g/mL for a period of time greater than or equal to that observed when an immediate release carprofen dosage form is dosed at any higher dose.

Most preferred oral controlled release carprofen dosage forms are those which are able to maintain plasma carprofen levels above approximately 10 $\mu$g/mL for a period of time greater than or equal to the time observed for an immediate release 2 mg/lb carprofen dosage form (10.5 hrs), when said oral controlled release carprofen dosage forms are administered at a dose less than 2 mg/lb. The performance of a 2 mg/lb oral immediate release dosage form is taken as the fundamental standard for purposes of this comparison since 2 mg/lb/day is the currently recommended and accepted efficacious oral dose in accordance with the present invention as described herein.

The term "implant" always denotes a solid pharmaceutical composition containing the chondroprotective compound of Formula (I), while the term "depot" usually implies a liquid pharmaceutical composition containing said compound of Formula (I), which is deposited in any suitable body tissues or cavities to form a reservoir or pool which slowly migrates to surrounding tissues and organs and eventually becomes systemically distributed. However, these distinctions are not always rigidly adhered to in the art, and consequently, it is contemplated that there is included within the scope of the present invention liquid implants and solid depots, and even mixed solid and liquid forms for each.

Other means of systemic administration which may utilize the chondroprotective compound of Formula (I) in either liquid or solid form include transdermal routes. In particular, transdermal patches prepared in accordance with well known drug delivery technology may be prepared and applied to the skin of a mammal to be treated, whereafter the active agent by reason of its formulated solubility characteristics migrates across the epidermis and into the dermal layers of the mammal's skin where it is taken up as part of the general circulation of the mammal, ultimately providing systemic distribution of the active ingredient over a desired, extended period of time. Also included are implants which are placed beneath the epidermal layer of the skin, i.e. between the epidermis and the dermis of the skin of the mammal being treated. Such an implant will be formulated in accordance with well known principles and materials commonly used in this delivery technology, and may be prepared in such a way as to provide controlled-, sustained-, and/or delayed-release of the active ingredient into the systemic circulation of the mammal. Such subepidermal (subcuticular) implants provide the same facility of installation and delivery efficiency as transdermal patches, but without the limitation of being subject to degradation, damage or accidental removal as a consequence of being exposed on the top layer of the mammal's skin.

Pharmaceutical compositions of special types suitable for oral administration to mammals may also be devised. Pharmaceutical compositions suitable for peroral administration, i.e., ingestion by mouth or administration through the mouth, may be solid or liquid. Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated. As is known in the art, the formulation of such palatable compositions takes into account mammal behavior regarding the extent of mastication of the dosage form which will take place, and the resultant level of dosing.

As with the other routes of administration and corresponding dosage forms described herein, dosage forms intended for oral administration are also suitably formulated to provide controlled-, sustained-, and/or delayed release of the active ingredient. Typically, these would include delayed-release oral tablets, capsules and multiparticulates, as well as enteric-coated tablets and capsules which prevent release and absorption of the active ingredient in the stomach of the mammal and facilitate enteric delivery distal to the stomach, i.e., in the intestines of the mammal. Other typical oral dosage forms would include sustained-release oral tablets, capsules, and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The description herein of the dosage forms which are contemplated to be within the scope of the present invention has, largely as a matter of convenience, classified such forms into those for local and systemic administration, as well as into solid and liquid forms. However, these distinctions are fairly arbitrary and should not be taken as in any way limiting the scope of the present invention with respect to routes of administration and dosage forms. For example, the description herein has already made it evident that some routes of administration, while ostensibly local, may also have systemic action or consequences. The line drawn herein between liquid and solid dosage forms may also be obscured in actual practice. For example, a suitable oral dosage form for use in the present invention includes encapsulated solutions, a mixed solid and liquid formulation. Microemulsion formulations, also within the scope of the present invention, may be characterized as a mixed solid and liquid dosage form.

The chondroprotective compound of Formula (I) can be administered locally to a joint in a mammal to be treated. Local vs. systemic administration entails a more focused vs. a more generalized manner of delivering the chondroprotective compound-containing pharmaceutical composition to a mammal in the early stages of articular cartilage degeneration. However, the use of depots and implants as well as delayed-, sustained-, and controlled-release formulations has tended to blur these distinctions. Accordingly, the above-described liquid and solid pharmaceutical compositions containing the chondroprotective compound of Formula (I) can, for the most part, be used for local administration as well, but with an emphasis on choosing components for said compositions which will tend to promote absorption of the compound of Formula (I) into the local tissues at the site of administration, but which will also tend to prevent infiltration and migration of the inhibitor into more outlying and distant tissues, resulting in systemic carryover.

Local administration is focused on suitable articular tissues into which the chondroprotective compound of Formula (I) may be injected, infused, implanted, deposited, inserted, or instilled. Such administration may include, but is not limited to, that which is intraarticular, intrachondrial, intracostal, intraligamentous, intramedulary, intramuscular, intraosteal, intrapelvic, intraspinal, intrasternal, intrasynovial, intratarsal, intrathecal, or intravenous.

Pharmaceutical compositions in liquid form containing the chondroprotective compound of Formula (I) offer the advantage of permitting injections of the liquid into or in close proximity to the articular site. By injection of the compound of Formula (I) directly into the joint, it is possible to achieve a high concentration of said compound in a short period of time, thus not only substantially enhancing access of said compound to the joint tissues, and thus the therapeutic activity of the compound of Formula (I), but also at the same time minimizing the occurrence of untoward adverse reactions that might otherwise occur. The result is a high local concentration of the compound of Formula (I) with a correspondingly low systemic carryover concentration.

Injections may also be made of pharmaceutical compositions containing the chondroprotective compound of Formula (I), where the pharmaceutical composition is in delayed-release, controlled-release, or sustained-release form. These formulations of recognized composition may be a solids, semi-solids, gels or other liquid/solid combinations in which an erodible matrix or series of coatings is used to provide a continuous release of the compound of Formula (I) at a predetermined rate or at variable rates if desired. The terms "extended-release" and "long-acting" as well as others are used to describe these formulations. All of these employ various combinations of bioerodible polymers, e.g., various cellulosic polymers, and natural materials, e.g., corn starch and magnesium stearate, to obtain slow and/or uniform dispensing of the compound of Formula (I) contained within the matrix. These pharmaceutical compositions may be injected into the articular site if suitably liquid or suspendable, or may be delivered by other means if more solid in nature.

The therapeutically effective amount for treating or preventing articular cartilage or subchondral bone degeneration or destruction, of the chondroprotective compound of Formula (I), is administered to a mammal being treated in an amount expressed as milligrams per kilogram of body weight of said mammal, per day: "mg/kg/day". The expression "per day" as used herein should not be interpreted as necessarily requiring that any particular dosage form be administered on a daily basis to the mammal being treated. The expression "per day" is merely an indication of the smallest convenient but arbitrary segment of time which is being used as part of the overall unit for measuring the dose of chondroprotective compound being administered. The dose, i.e., the therapeutically effective amount of a compound of Formula (I) for treating or preventing articular cartilage or subchondral bone degeneration or destruction will usually range from about 0.01 mg/kg/day to about 20.0 mg/kg/day, preferably from about 0.1 mg/kg/day to about 12.0 mg/kg/day, more preferably from about 0.5 mg/kg/day to about 10.0 mg/kg/day, and most preferably from about 0.5 mg/kg/day to about 8.0 mg/kg/day. For instance, a 50 lb. mammal weighs 23 kg (1 kg=2.2 lb.), and thus would be treated most preferably with from about 10 mg to about 180 mg of therapeutic agent per day. The fractional amounts are not significant and the dosages would appropriately be rounded to a number which corresponds to unit dosage amounts which are conveniently available. Where the dosage form is, e.g., an injectable liquid, the preferred dosage amounts may be achieved more precisely. On the other hand, where the dosage form is, e.g., an oral tablet, it will be necessary to make more of an approximation of the preferred dosage. Thus, the 10 mg dose could be approximated by halving a 25 mg tablet, and the 180 mg dose could be approximated by using a 100 mg tablet together with a 75 mg tablet or three 25 mg tablets, since these are typical dosage amounts for oral tablets. As will be apparent to those skilled in this art, where the dosage form most frequently employed is the oral tablet and a large number of mammals are treated on a daily basis, added convenience will be obtained through the use of a dispenser containing all of the available dosage amounts of said tablets, e.g., 25 mg, 75 mg, and 100 mg tablets. In this way virtually any preferred dosage amount may be approximated using a combination of said tablets and/or halves thereof.

It is necessary for the skilled artisan, such as a veterinarian, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy. However, this generalization does not take into account such important variables as the specific type of articular cartilage or subchondral bone degeneration or destruction involved, the specific therapeutic agent involved and its pharmacokinetics, and the specific patient (mammal) involved. For an approved product in the marketplace, much of this information is already provided by the results of clinical studies carried out to obtain such approval. In other cases, such information may be obtained in a straightforward manner in accordance with the teachings and guidelines contained in the instant specification taken in light of the knowledge and skill of the artisan. The results which are obtained can also be correlated with data from corresponding evaluations of an approved product in the same assays.

The above-recited ranges of dosage amounts, which are also recited elsewhere herein, are for racemic mixtures of compounds of Formula (I) having a chiral carbon, or for single compounds of Formula (I) where no chiral carbon atom is present. As will be appreciated by the person of ordinary skill in this art, i.e., a practicing veterinarian or a person with an advanced degree and experience in animal health issues, where other than a racemic mixture of compounds of Formula (I) is involved, the chondroprotective therapeutically effective amount will vary. For example, if 85% of the mixture is (S)-enantiomer, that will ordinarily tend to reduce the necessary dosage. These considerations are based on an assumed equal potency, and the fact that the (S)-enantiomer is significantly more active than the (R)-enantiomer. However, the degree of difference between the activities of the two enantiomers must also take into account other differences, especially differences in pharmacokinetics between the two enantiomers, in determining the proper dosage. For example, it has been found that there is a significant difference in clearance rates between the (+)(S) and (-)(R) enantiomers. This, in turn, will have a calculable impact on the amount of active compound to be administered. Ordinarily, such determinations will be made on a case-by-case basis by the artisan, but these are well within the ordinary skill of the art, as is instituting the methods whereby data necessary for the supporting calculations may be obtained.

Typical dosage forms and amounts would include (1) intravenous administration of carprofen at a dose rate of 4.0 mg/kg/day of bodyweight, injected into the right cephalic vein; (2) oral administration of carprofen at a dose rate of 4.0 mg/kg/day of bodyweight as an oral paste syringed on the back of the tongue, given one hour before feeding; and (3) oral administration of carprofen at a dose rate of 4.0 mg/kg/day of bodyweight as 25 mg, 75 mg, and 100 mg tablet preparations, placed on the back of the tongue of the mammal being treated, given one hour before feeding.

The active ingredients of the present invention may also be combined with other therapeutically active ingredients which would be readily apparent to the skilled artisan in this field, and which will usually be determined by the circumstances under which the therapeutic agent of the present invention is administered. For example, where a joint has become seriously infected at the same time by microorganisms, e.g., bacteria, fungi, protozoa, virus and the like, the active ingredient of the present invention will desirably be administered in combination with one or more antibiotic, antifungal, antiprotozoal, antiviral or similar therapeutic agents. The active ingredient of the present invention may be administered in combination with NSAIDs as well with inhibitors of other mediators of inflammation. Additional classes of such inhibitors and examples thereof include, e.g., $H_1$ -receptor antagonists; kinin-$B_1$- and $B_2$ -receptor antagonists; prostaglandin inhibitors such as PGD-, PGF- $PGI_2$ -, and PGE-receptor antagonists; thromboxane $A_2$ (TXA2-) inhibitors; 5- and 12-lipoxygenase inhibitors; leukotriene $LTC_4$ -, $LTD_4/LTE_4$ -, and $LTB_4$ -inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids, e.g., dexamethasone; broad-spectrum antiparasitic antibiotics, e.g., the avermectins and the milbemycins; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The class of therapeutic agents which are broad-spectrum antiparasitic antibiotics, e.g., the avermectins and the milbemycins, are especially good candidates for co-administration and other types of combination therapy with the chondroprotective compounds of Formula (I), since these endo- and ecto-parasiticides are administered on a chronic basis to mammals, especially to cats and dogs for the treatment of serious parasitic infestations. One of the most significant of these is heartworm, which is a very damaging and often fatal parasitic affliction of cats and dogs. The avermectins are a class of pentacyclic 16-membered lactones related in structure to the milbemycins, and are isolated from cultures of *Streptomyces avermitilis*. Specific agents include avermectin $A_{1a/b'}$, avermectin $A_{2a/b'}$, avermectin $B_{1a/b'}$, and avermectin $B_{2a/b'}$. The avermectins are described in more detail in U.S. Pat. No. 4,310,159, which is incorporated herein by reference in its entirety. The milbemycins are a family of novel macrolide antibiotics with insecticidal and acaricidal activity, and are isolated from cultures of *Streptomyces hygroscopicus*. The milbemycins are described in more detail in U.S. Pat. No. 3,950,360, which is incorporated herein by reference in its entirety. Yet another family of compounds included within the scope of the broad-spectrum antiparisitic antibiotics, is one related in chemical structure and biological activity to the avermectins and the milbemycins, which may be represented by Formula (II):

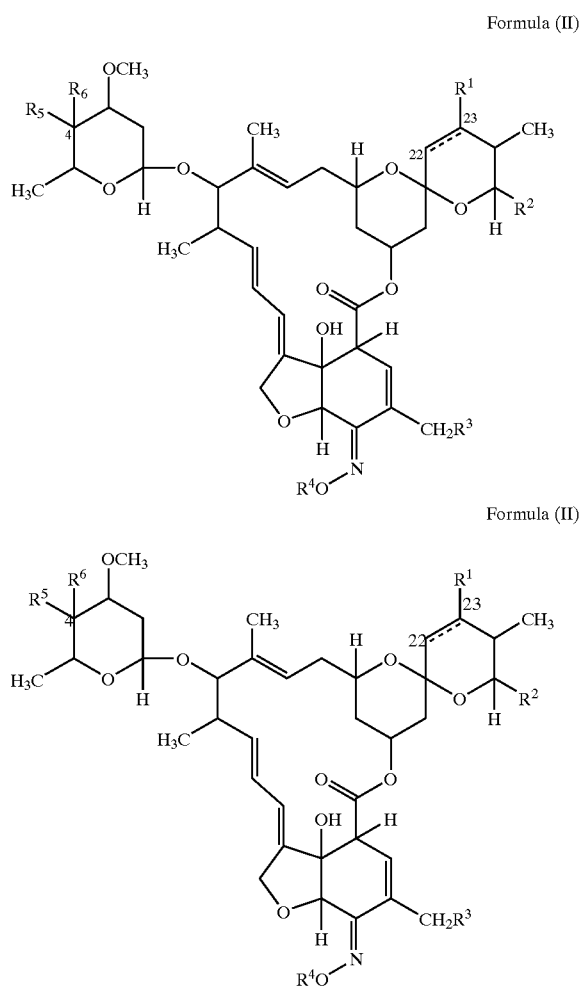

Formula (II)

Formula (II)

This family of macrolides is described in more detail in WO 94/15944 and EP 0677054, both of which are incorporated herein by reference in their entireties.

Because the early stages of articular cartilage degeneration are prevalent among geriatric mammals, it will be appreciated by those skilled in the art that the chondroprotective compounds of Formula (I) may also be administered in combination with therapeutic agents intended for the treatment of disease conditions, syndromes and symptoms which are also found in abundance in older mammals. Such therapeutic agents and the conditions which they are used to treat include, e.g., cognitive therapeutics to counteract memory loss and impairment; and antidyskinetic/antiparkinsonian agents, e.g., selegeline.. Another large class of such therapeutic agents includes anti-hypertensives and other cardiovascular drugs intended to offset hypertension, myocardial ischemia including angina, congestive heart failure, and myocardial infarction, e.g., diuretics, vasodilators such as hydralazine, β-adrenergic receptor antagonists such as propranolol, angiotensin-II converting enzyme inhibitors (ACE-inhibitors) such as enalapril used to treat geriatric mammals with mitral insufficiency, and enalapril alone and in combination with neutral endopeptidase inhibitors, angiotensin II receptor antagonists such as losartan, renin inhibitors, calcium channel blockers such as nifedipine, sympatholytic agents such as methyldopa, $\alpha_2$-adrenergic agonist such as clonidine, $\alpha$-adrenergic receptor antagonists such as prazosin, and HMG-CoA-reductase inhibitors (anti-hypercholesterolemics) such as lovastatin.

Still other classes of such therapeutic agents include antineoplastic agents, especially antimitotic drugs including the vinca alkaloids such as vinblastine and vincristine, for treating various cancers; therapeutic agents for treating renal failure; anti-obesity drugs for treating excess weight problems in mammals; anti-parasitic drugs for treating both endo- and ecto-parasites which commonly afflict mammals; and anti-pruritic drugs for treating various types of pruritis in mammals.

Other types of drugs which can be used in combination with the anti-inflammatory agents of the present invention include growth hormone secretagogues; strong analgesics; local and systemic anesthetics; and $H_2$-receptor antagonists and other gastroprotective agents. It will be recognized by those of ordinary skill in this art that some of the above combinations of therapeutic agents will be used most frequently to treat various acute conditions in mammals, e.g., bacterial infections occurring simultaneously with degenerative joint disease. However, there would be an equal if not greater interest on the part of such skilled persons in treating chronic conditions in mammals.

In accordance with a regimen which would be used for this purpose, it is contemplated that the chondroprotective compounds of Formula (I) would be administered in combination with other medications used on a regularly scheduled basis for treating chronic conditions such as hyperlipidemia. It is also envisioned that administration in combinations could assume a number of different forms and still be within the scope of the present invention. For example, the chondroprotective compounds of Formula (I) might simply be formulated with one or more of the other therapeutic agents which are to form the intended combination, into a convenient dosage form, such as an oral tablet, containing all of the drugs forming the combination. Varying half-lives for the different drugs could be accommodated by the person skilled in preparing formulations by creating controlled-release forms of said drugs with different release times so that relatively uniform dosing was achieved. A medicated feed used as the dosage form could also be prepared in accordance with well known principles in the art of formulation, in which the drugs used in the combination were simply present together in admixture in the feed composition. The present invention also contemplates co-administration in which the combination of drugs is achieved by the simultaneous administration of the drugs to be given in combination. Such co-administration could even be by means of different dosage forms and routes of administration. The present invention further contemplates the use of such combinations in accordance with different but regular and continuous dosing schedules whereby desired plasma levels of the drugs involved were maintained in the mammal being treated, even though the individual drugs making up the combination were not being administered to said mammal simultaneously. All such combinations would be well within the skill of the art to devise and administer.

As above-described, the method of the present invention comprises two basic steps: (I) establishing the status of a candidate mammal as presently or prospectively being in the early stages of degeneration of articular cartilage or subchondral bone in one or more joints of said mammal, thereby confirming that said mammabl is in need of such treatment; and thereupon (II) treating or preventing said early stages by administering to said mammal an amount therapeutically effective for treating or preventing said early stages of degeneration of articular cartilage or subchondral bone, of a chondroprotective compound of Formula (I). The various aspects of Step (II) have already been discussed above in detail. Accordingly, the aspects of Step (I) will now be discussed in detail.

It is necessary to establish the status of a mammal which is a candidate for treatment in accordance with the present invention as to whether or not the mammal is presently or prospectively in the early stages of degeneration of articular cartilage or subchondral bone in one or more joints of said mammal. The expression "presently or prospectively" as used herein is intended to mean that in accordance with the below-discussed methods of making that determination, it is possible to identify a candidate mammal as either being presently in need of such treatment, or as very likely or expected to be in need of such treatment in the short term future. Prospective need of treatment may be established by those determinations of positive factors which from the experience of the artisan lead directly to the early stages of articular cartilage and subchondral bone degeneration. For example, the artisan may establish from clinical examination of a mammal, especially a dog, that it has incipient hip dysplasia, and may confirm this conclusion with radiographic evidence from which it may be determined in accordance with established methods of measurement that the dog will develop hip dysplasia within the short term future.

Thus the need for treatment may be determined by (1) positive results from the clinical arthroscopic examination and evaluation of the joints of the candidate mammal. The diagnosis of incipient or realized hip dysplasia has already been discussed. Other clinical symptomology and signs would include those gained from direct examination of the joints of the candidate mammal.

The skilled artisan would also be aware that (2) performance of any invasive surgical procedure on one or more joints of the candidate mammal would be under most circumstances sufficient reason by itself to conclude that treatment was needed. This follows from the fact that invasive surgery on the joint of a mammal, especially a dog, inevitably degrades the ability of that joint to bear its accustomed load as efficiently as before surgery. The increased mechanical stress on the joint would, in the experience of the artisan, lead directly to the early stages of articular cartilage and subchondral bone degeneration. Such surgery on the joint would also produce an effusion of blood and other fluids containing cytokines and other factors which are causative agents of inflammation, and would thereby permit their migration and absorption into the solid tissues of the joint, including the cartilage and subchondral bone. The artisan would appreciate that this would also lead directly to the early stages of articular cartilage and subchondral bone degeneration.

Further, the need for treatment may be determined or confirmed by (3) positive results from an examination of one or more joints of said mammal using noninvasive procedures including radiographic and magnetic resonance imaging (MRI). The latter technique is better for evaluating soft tissues than is the former. MRI is a technique for multiplanar body imaging that shows increased soft tissue contrast resolution. Since MRI can visualize soft tissue changes, it is suitable for imaging the pathology of the early changes in articular cartilage and subchondral bone degeneration.

The need for treatment may also be determined or confirmed by (4) positive results from any biochemical test performed on body fluids or joint tissue of the candidate mammal with respect to one or more of the following substances: increased interleukin-1 beta (IL-1$\beta$); increased tumor necrosis factor alpha (TNF$\alpha$); increased ratio of IL-1$\beta$ to IL-1 receptor antagonist protein (IRAP); increased expression of p55 TNF receptors (p55 TNF-R); increased interleukin-6 (IL-6); increased leukemia inhibitory factor (LIF); unchanged or decreased insulin-like growth factor-1 (IGF-1); decreased transforming growth factor beta (TGF$\beta$); unchanged or decreased platelet-derived growth factor (PDGF); unchanged or decreased basic fibroblast growth factor (b-FGF); increased keratan sulfate; increased stromelysin; increased ratio of stromelysin to tissue inhibitor of metalloproteases (TIMP); increased osteocalcin; increased alkaline phosphatase; increased cAMP responsive to hormone challenge; increased urokinase plasminogen activator (uPA); increased cartilage oligomeric matrix protein; and increased collagenase.

DESCRIPTION OF PREFERRED EMBODIMENTS

In order to further demonstrate the methods and compositions of the present invention, there is presented in the paragraphs which follow specific descriptive examples of typical procedures which may be employed in carrying out said methods. However, said examples are intended to be illustrative only and should not be taken as in any way a limitation of the present invention, for which purpose the present claims are appended hereto.

EXAMPLE 1

Three groups of skeletally mature crossbred mammals, weighing 20 to 25 kg each, are used in a study whose objective is to demonstrate subchondral bone changes which are a marker for the early stages of articular cartilage degeneration in mammals, and which, accordingly, may be used to identify mammals which are appropriate candidates for pharmacologic intervention.

In Group I, osteoarthritis is induced in these mammals (n=4) using the surgical procedure described in Pelletier, J.-P.; Martel-Pelletier, J.; Altman, R. D.; Ghandur-Mnaymneh, L.; Howell, D. S.; Woessner, J. F., Jr.; "Collagenolytic Activity and Collagen Matrix Breakdown of the Articular Cartilage in the Pond-Nuki Mammal Model of Osteoarthritis", *Arthritis Rheum*, 26, 1983, 866–874; wherein said mammals are anesthetized with intravenous injection of sodium pentobarbital (25 mg/kg), and the anterior cruciate ligament of the right knee is sectioned by a stab incision. After surgery the mammals are housed and allowed to exercise ad libitum. The mammals are administered carprofen, 6-chloro-$\alpha$-methyl-9H-carbazole-2-acetic acid, at a dose of 2.2 mg/kg bid po for 8 weeks, beginning 4 weeks after surgery The right knees of unoperated mammals (n=4) serve as normal controls. Groups II and III (n=4, each group) are operated on in the same manner, but receive no treatment. The mammals in Groups I and II are killed by intravenous overdose of Nembutal at 12 weeks after surgery, while the mammals in Group III are killed in the same manner at 4 weeks after surgery. Normal mammals are also used as control.

The proximal end of the tibia is removed as below-described, rinsed in a cold physiological saline solution, and placed on ice prior to and throughout dissection. Normal bone specimens are obtained from plug explants of medial tibial plateaus collected at dissection. Medial tibial plateaus are extracted to prepare explants and primary bone cell cultures; no marginal cortical bone tissue is included. The overlying cartilage is first removed from the tibial plateaus, and plug explants are dissected out exclusively from the midportion of the medial plateau. The trabecular bone tissue is then dissected away from the subchondral bone plate. All manipulations are performed under a magnifying microscope to ensure complete removal of cartilage and trabecular bone. The subchondral bone plate of the tibial plateau specimens is then separated into 2 portions. The subchondral bone specimens from the normal mammals are observed to be consistently thinner than those of the osteoarthritis mammals, which are also observed to have evident sclerosis.

The first group of specimens is used to prepare ex vivo bone samples of 100–200 mg wet weight for explant culture. Explants are washed 3 times by vortexing samples in serum-free BGJ medium (Sigma, St. Louis, Mo.), and are cultured in the same medium at 37° C. in a humidified atmosphere with 5% $O_2$/95% $CO_2$. Conditioned media are recovered after 5 days of culture under these conditions, and stored at −80° C. prior to assay.

The second portion of the samples is used to prepare primary cell cultures as described in Lajeunesse, D.; Busque, L.; Menard, P.; Brunette, M. G.; Bonny, Y.; "Demonstration of an Osteoblast Defect in Two Cases of Human Malignant Osteoporosis: Correction of the Phenotype after Bone Marrow Transplant"; *J. Clin Invest*, 98, 1996, 1835–1842, with minor modifications. Bone samples are cut into small pieces (2 mm$^2$) prior to their sequential digestion in the presence of 1 mg/ml type I collagenase (Sigma) in Ham's F-12/Dulbecco's modified Eagle's medium (DMEM; Sigma) without serum, at 37° C. for 20, 20, and 240 minutes. This treatment removes both adherent and remaining bone marrow cells from the cortical bone pieces.

After washing with the same medium, the digested bone pieces are cultured in BGJ medium containing 20% fetal bovine serum (FBS; Wisent, St. Bruno, Quebec, Canada). This medium is replaced every 2 days until cells are observed in the Petri dishes, at which time the culture medium is replaced with fresh medium containing 10% FBS. At confluence, cells are passaged once at a ratio of 25,000 cells/cm$^2$ and are grown in 24-well plates (Falcon, Lincoln Park, N.J.) for 5 days prior to assay. Cells obtained under these culture conditions show an osteoblast-like cell phenotype, as noted in the above-mentioned article from the scientific literature by Lajeunesse et al. Conditioning is performed for the last 2 days of culture, in the presence or absence of 50 nM 1,25(OH)$_2$D$_3$ (1,25-dihydroxyvitamin D) for maximal stimulation, in Ham's F-12/DMEM containing 2% charcoal-stripped FBS, which yields maximal stimulation of alkaline phosphatase activity and osteocalcin secretion, as noted in the above-mentioned article from the scientific literature by Lajeunesse et al. The medium is collected at the end of the incubation and frozen at −80° C. prior to assay. Cells are then washed twice with phosphate buffered saline (PBS), pH 7.4, and solubilized in alkaline phosphatase buffer (100 mM glycine, 1 mM MgCl$_2$, 1 mM ZnCl$_2$, 1% Triton X-100; pH 10.5) for 60 minutes with agitation at 4° C.

For cAMP determination, cells are preincubated for 15 minutes in the presence of a phosphodiesterase inhibitor (1 mM 3-isobutyl-1-methylxanthine; Sigma), in Ham's F-12/ DMEM containing 0.5% bovine serum albumin (fatty acid-free fraction V; Sigma). At the end of the preincubation, the cells are incubated for 5 minutes in the same medium, containing either 100 nM human parathyroid hormone fragment 1–34 (PTH; Penninsula, Belmont, Calif.), 5 nM prostaglandin E$_2$ (PGE$_2$; Sigma), 1 µM forskolin (Sigma), or vehicle, and the reaction is stopped with 3% perchloric acid (final concentration). Cyclic AMP levels are then evaluated by radioimmunoassay (Diagnostic Products, Los Angeles, Calif.) as described in Lajeunesse, D.; Kiebzak, G. M.; Frondoza, C.; Sacktor, B.; "Regulation of Osteocalcin Secretion by Human Primary Bone Cells and by the Human Osteosarcoma Cell Line MG-63, *Bone*, 14, 1991, 237–250.

Osteocalcin release is measured in conditioned Ham's F-12/DMEM (1:1) prepared for the last 2 days of culture of osteoblast-like cells as described in the above-mentioned article from the scientific literature by Lajeunesse et al., containing 2% charcoal-treated FBS, and in the presence of 50 nM 1,25(OH)$_2$D$_3$ or vehicle (0.1% ethanol). Nascent osteocalcin is determined using a specific enzyme immunoassay (Biomedical Technologies, Stoughton, Mass.). The detection limit of this assay is 0.5 ng/ml, and 2% charcoal-treated FBS contains <0.1 ng/ml osteocalcin. Cellular alkaline phosphatase activity is determined, on cells used for osteocalcin release, as the release of p-nitrophenol hydrolyzed from p-nitrophenyl phosphate (12.5 mM final concentration) at 37° C. for 30 minutes after solubilizing the cells in alkaline phosphatase buffer as above-described. Alkaline phosphatase is determined immediately on aliquots. Protein determination is performed by the bicinchoninic acid method described in Smith, P. K.; Krohn, R. I.; Hermanson, G. T.; Mallia, A. K.; Gartner, F. H.; Provenzano, M. D.; et al; "Measurement of Protein Using Bicinchoninic Acid", *Anal Biochem*, 150, 1985, 76–85.

For evaluation of uPA, PAI-1, and IGF-1, there is used conditioned media from subchondral bone explants (100–200 mg wet weight per explant tested, 5 days of conditioning) and from confluent osteoblast-like cells fed with Ham's F-12/DMEM, without PBS, but containing 1% insulin-transferrin-selenium mix (ITS, Sigma) for the last 2 days of culture. First, uPA levels are determined by specific enzyme-linked immunosorbent assay (ELISA; American Diagnostica, Greenwich, Conn.). There is then used the procedure described in Leprince, P.; Rogister, B.; Moonen, G. A.; "Colorimetric Assay for the Simultaneous Measurement of Plasminogen Activators and Plasminogen Ativator Inhibitors in Serum-Free Conditioned Media from Cultured Cells", *Anal Biochem*, 177, 1989, 341–346, to determine the activity of uPA via the hydrolysis of the specific substrate DL-Val-Leu-Arg-p-nitroanilide (Sigma), which releases p-nitroaniline that can be detected at 405 nm. PAI-1 levels are determined by ELISA, using materials available from American Diagnostica (Greewich, Conn.). IGF-1 is determined using a high-sensitivity ELISA (Diagnostic Systems Laboratories, Webster, Tex.) that does not cross-react with insulin. Internal control studies are performed with the media alone containing 1% ITS, and any values obtained should be below the limit of detection. For the conditioned medium of bone explants, samples are processed directly, whereas for cell culture samples, 3 or 4 supernatants are pooled, lyophilized, and then reconstituted in PBS buffer, pH 7.4. Samples are then treated according to the method described in Mohan, S.; Bautista, C. M.; Herring, S. J.; Linkhart, T. A.; Baylink, D. J.; "Development of Valid Methods to Measure Insulin-Like Growth Factors-I and -II in Bone Cell-Conditioned Medium, *Endocrinology*, 126, 1990, 2534–42.

The results of the above evaluations confirm their detectability and ability to establish the existence of the early stages of articular cartilage and subchondral bone degeneration in mammals.

What is claimed is:

1. A method of treating or preventing the early stages of degeneration of articular cartilage or subchondral bone in one or more joints of a mammal in need of such treatment, comprising determining a mammal as being in an early stage, without clinical symptoms, of degeneration of articular cartilage or subchondral bone in one or more joints; and administering to the mammal, prior to onset of clinical symptoms associated with the degeneration of articular cartilage or subchondral bone, an amount therapeutically effective for treating or preventing the early stage of degeneration of articular cartilage or subchondral bone, of a chondroprotective compound of Formula (1):

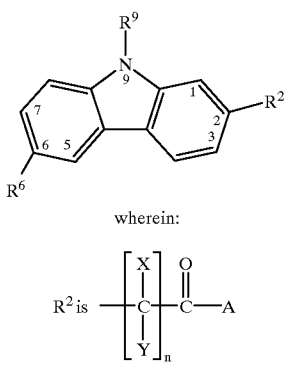

Formula (I)

wherein:

$R^2$ is $-\begin{bmatrix} X & O \\ | & \| \\ -C-C-A \\ | \\ Y \end{bmatrix}_n$ where A is hydroxy, $(C_1-C_4)$alkoxy, amino, hydroxy-amino, mono-$(C_1-C_2)$alkylamino, di-$(C_1-C_2)$alkylamino; X and Y are independently H or $(C_1-C_2)$alkyl; and n is 1 or 2;

$R^6$ is halogen, $(C_1-C_3)$alkyl, trifluoromethyl, or nitro;

$R^9$ is H; $(C_1-C_2)$alkyl; phenyl or phenyl-$(C_1-C_2)$alkyl, where phenyl is optionally mono-substituted by fluoro or chloro; —C(=O)—R, where R is $(C_1-C_2)$alkyl or phenyl, optionally mono-substituted by fluoro or chloro; or —C(=O)—O—$R^1$, where $R^1$ is $(C_1-C_2)$alkyl;

where X and Y are different, the (−)(R) and (+)(S) enantiomers thereof; and all pharmaceutically acceptable salt forms, prodrugs and metabolites thereof which are therapeutically active for treating or preventing the early stages of degeneration of articular cartilage or subchondral bone.

2. A method according to claim 1 wherein said chondroprotective compound of Formula (I) exists as (−)(R) and (+)(S) enantiomers, and said (+)(S) enantiomer is used alone.

3. A method according to claim 1 wherein said mammal is a cat, dog or horse, and said treatment or prevention ameliorates, diminishes, actively treats, reverses or prevents any injury, damage or loss of articular cartilage or subchondral bone subsequent to said early stage of said degeneration.

4. A method according to claim 1 wherein said status of said mammal as presently or prospectively being in said early stages and thus in need of such treatment is determined by one or more of the following:

(A) positive results from the clinical examination and evaluation of the joints of said mammal, including measurement of hip dysplasia progression;

(B) performance of any invasive surgical procedure on one or more joints of said mammal;

(C) positive results from an examination of one or more joints of said mammal using noninvasive procedures including radiographic and magnetic resonance imaging (MRI); and (D) positive results from any biochemical test performed on body fluids or joint tissue of said mammal with respect to one or more of the following substances:

(1) increased interleukin-1 beta (IL-1β);

(2) increased tumor necrosis factor alpha (TNFα);

(3) increased ratio of IL-β to IL-1 receptor antagonist protein (IRAP);

(4) increased expression of p55 TNF receptors (p55 TNF-R);

(5) increased interleukin-6 (IL-6); increased leukemia inhibitory factor (LIF);

(6) unchanged or decreased insulin-like growth factor-1 (IGF-1);

(7) decreased transforming growth factor beta (TGFβ); unchanged or decreased platelet-derived growth factor (PDGF);

(8) unchanged or decreased basic fibroblast growth factor (b-FGF);

(9) increased keratan sulfate;

(10) increased matrix metalloproteases (MMPs) including stromelysin;

(11) increased ratio of matrix metalloproteases (MMPs) including stromelysin, to tissue inhibitor of metalloproteases (TIMP);

(12) increased osteocalcin;

(13) increased alkaline phosphatase;

(14) increased cAMP responsive to hormone challenge;

(15) increased urokinase plasminogen activator (uPA);

(16) increased cartilage oligomeric matrix protein;

(17) presence of type-II specific collagen neoepitopes and

(18) increased collagenase.

5. A method according to claim 1 additionally including administering combinations of compounds, comprising:

(A) more than one member selected from the group of chondroprotective compounds of Formula (I); or (B) one or more of said chondroprotective compounds of Formula (I) administered together with one or more members selected from the group consisting essentially of polysulfated glycosaminoglycan (PSGAG), glucosamine, chondroitin sulfate (CS), hyaluronic acid (HA), pentosan polysulfate (PPS), doxycycline, and minocycline.

6. A method according to claim 1 wherein said chondroprotective compound is 6-chloro-α-methyl-9H-carbazole-2-acetic acid and said administered amount is about 2.0 mg/kg/day to about 4.0 mg/kg/day.

* * * * *